(12) United States Patent
Herman

(10) Patent No.: US 7,347,943 B2
(45) Date of Patent: *Mar. 25, 2008

(54) METHODS AND COMPOSITIONS FOR CHROMATOGRAPHY

(75) Inventor: Heath H. Herman, Tucker, GA (US)

(73) Assignee: Kinetic Biosystems Inc., Durham, NC (US)

( * ) Notice: Subject to any disclaimer, the term of this patent is extended or adjusted under 35 U.S.C. 154(b) by 314 days.

This patent is subject to a terminal disclaimer.

(21) Appl. No.: 11/214,144

(22) Filed: Aug. 29, 2005

(65) Prior Publication Data

US 2006/0000779 A1 Jan. 5, 2006

Related U.S. Application Data

(63) Continuation of application No. 10/293,916, filed on Nov. 12, 2002, now Pat. No. 6,942,804.

(60) Provisional application No. 60/344,745, filed on Nov. 9, 2001.

(51) Int. Cl.
*B01D 15/08* (2006.01)
(52) U.S. Cl. ............... 210/657; 210/656; 210/198.2
(58) Field of Classification Search .............. 210/656, 210/657, 658, 198.2
See application file for complete search history.

(56) References Cited

U.S. PATENT DOCUMENTS

| | | | |
|---|---|---|---|
| 4,279,753 A | 7/1981 | Nielson et al. | |
| 4,422,941 A | 12/1983 | Vaughan et al. | |
| 4,632,762 A | 12/1986 | Ramsland | |
| 4,783,326 A | 11/1988 | Srednicki | |
| 4,857,187 A | 8/1989 | Ito | |
| 4,900,446 A | 2/1990 | Anderson | |
| 5,273,656 A | 12/1993 | Anderson et al. | |
| 5,328,673 A | 7/1994 | Kaczur et al. | |
| 5,622,819 A | 4/1997 | Herman | |
| 5,821,116 A | 10/1998 | Herman | |
| 6,133,019 A | 10/2000 | Herman | |
| 6,214,617 B1 | 4/2001 | Herman | |
| 6,280,696 B1 | 8/2001 | Hsu et al. | |
| 6,916,652 B2 | 7/2005 | Petrecca et al. | |
| 6,942,804 B2 | 9/2005 | Herman | |
| 2001/0044143 A1 | 11/2001 | Herman et al. | |
| 2002/0061270 A1 | 5/2002 | Osborne | |
| 2003/0054546 A1 | 3/2003 | Petrecca et al. | |
| 2003/0064428 A1 | 4/2003 | Herman et al. | |

FOREIGN PATENT DOCUMENTS

WO   WO 90/05572 A   5/1990

OTHER PUBLICATIONS

Search Report PCT/US02/36497, May 23, 2005, Kinetic BioPharma Inc.

*Primary Examiner*—Ernest G. Therkorn
(74) *Attorney, Agent, or Firm*—Troutman Sanders LLP

(57) ABSTRACT

The present invention is directed to methods and compositions for separating and isolating target molecules. In particular, the present invention comprises devices, such as CCDs, that contain particles without the need for support structures. Chromatography separation techniques, including but not limited to, ion exchange, size separation, affinity chromatography, ion exclusion, ligand exchange, reversed phase and normal phase partitioning, are used in the CCD. Methods also include low, medium and high pressure liquid chromatography. Such methods can be used for analytical, semi-preparative processes, initial clarification, preparative filtration and process scale applications.

17 Claims, 24 Drawing Sheets

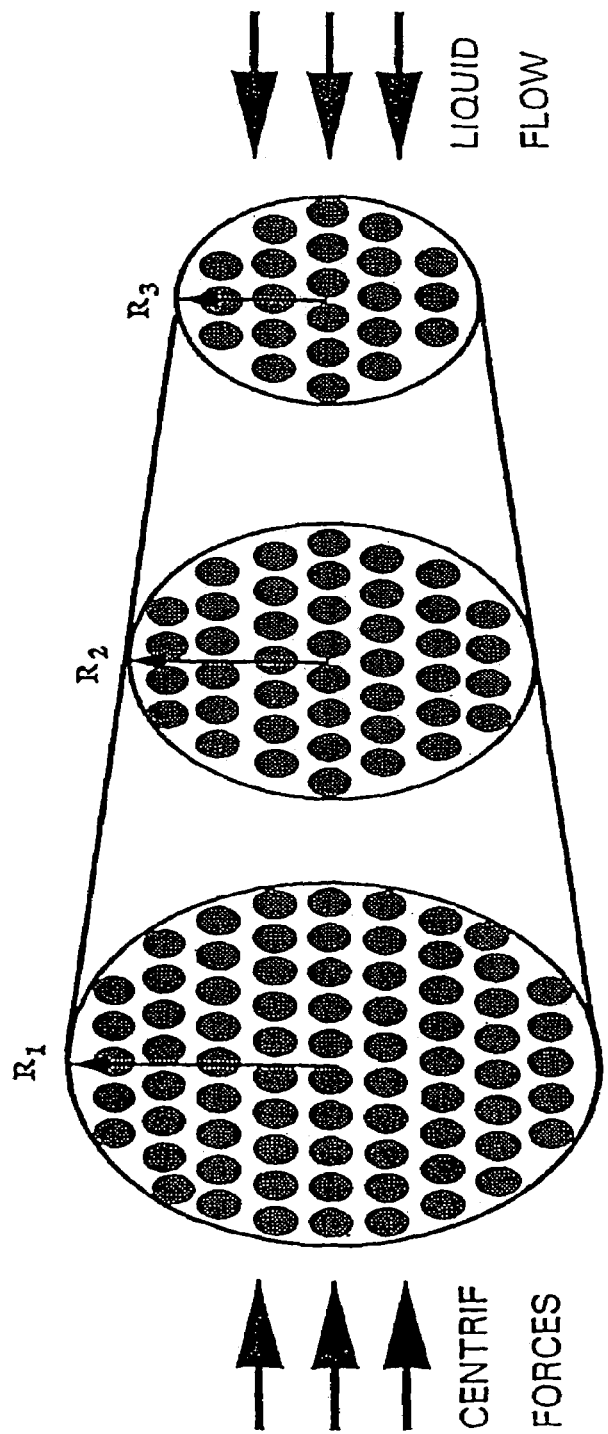
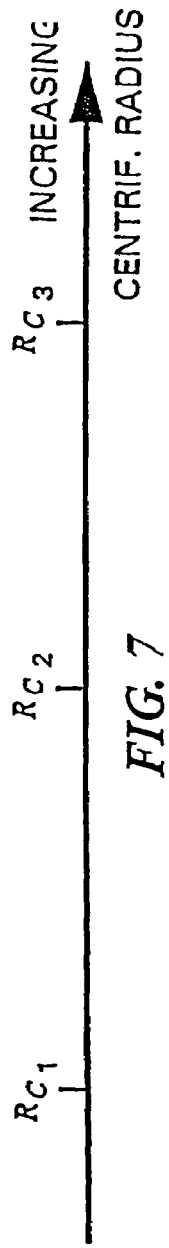
$$\text{Flow Velocity} = \frac{\text{Flow Rate}}{\Upsilon \times R_x^2} \quad (1)$$
$$\text{Relative Centrifugal Force} = w^2 R_{C_x} \quad (2)$$
FIG. 7

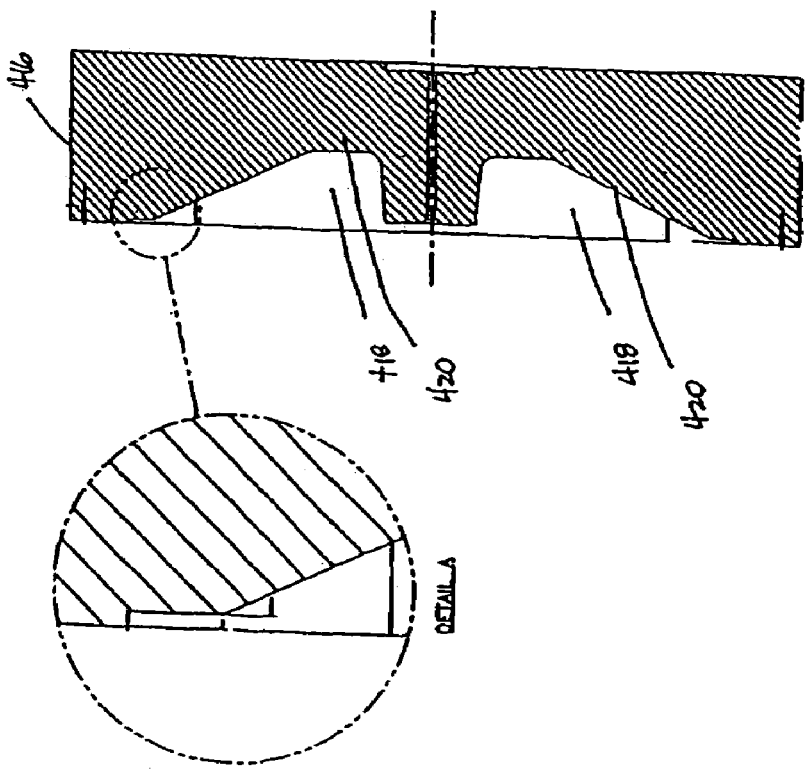
FIG. 18B SECTION B-B
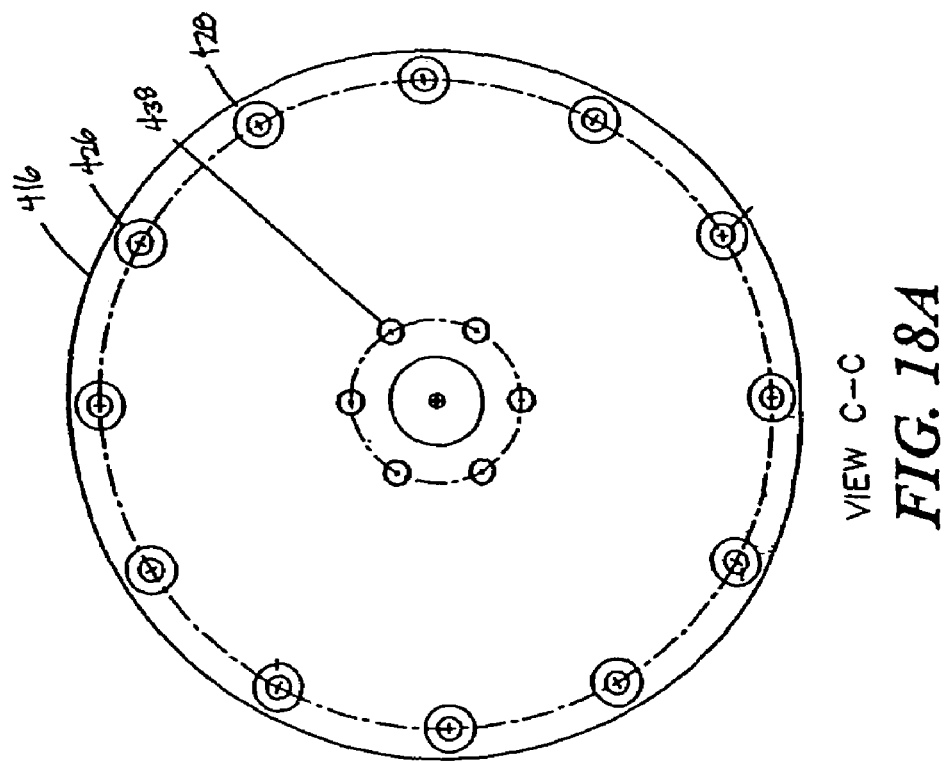
FIG. 18A VIEW C-C

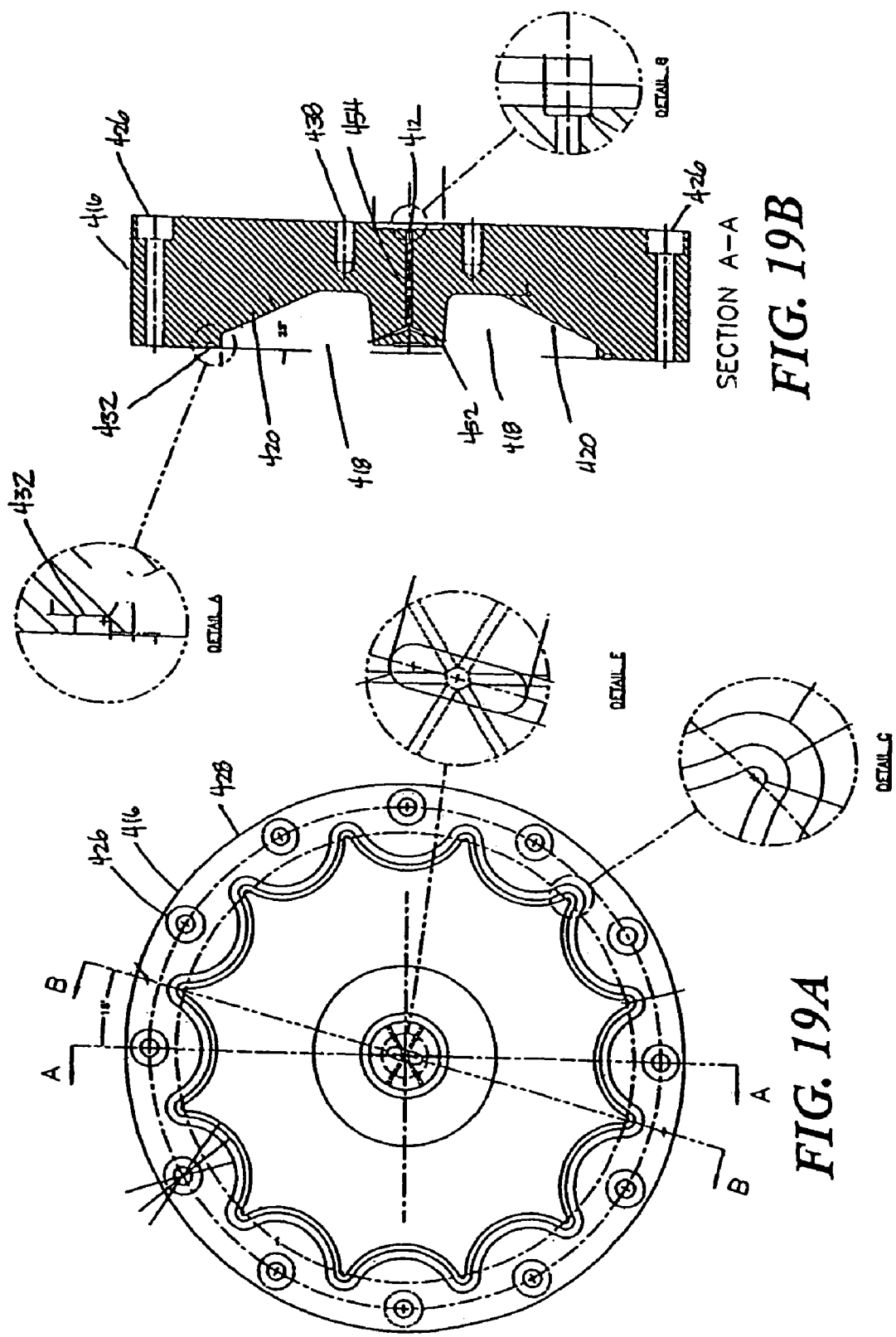

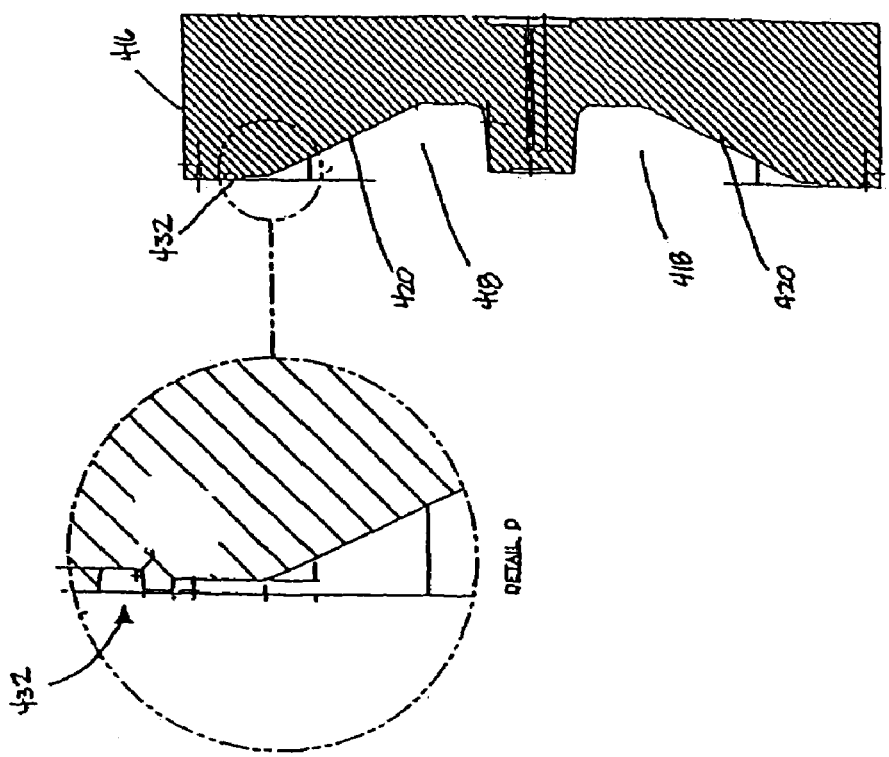
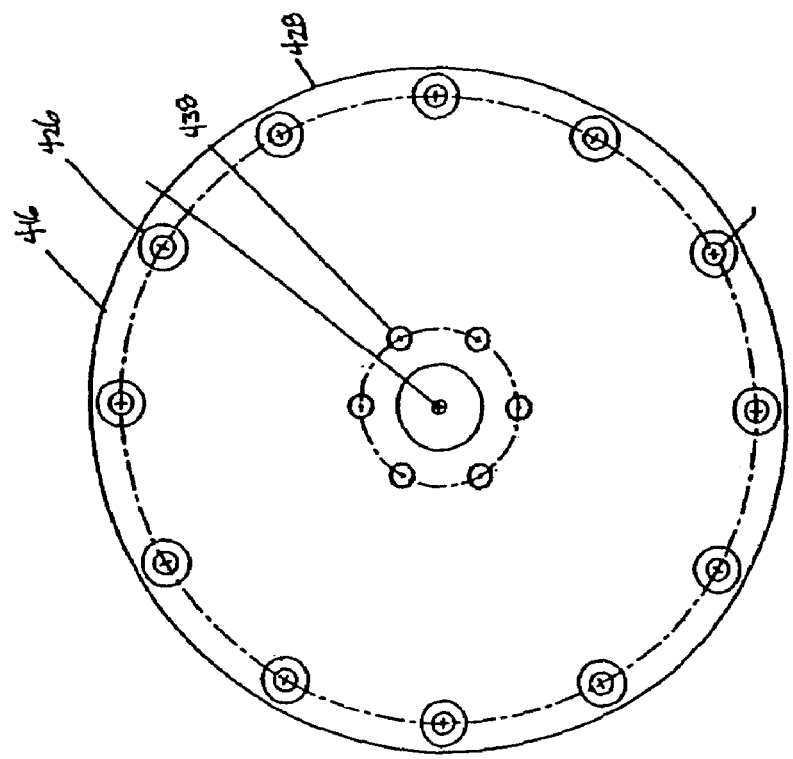
FIG. 20B SECTION B-B
FIG. 20A VIEW C-C

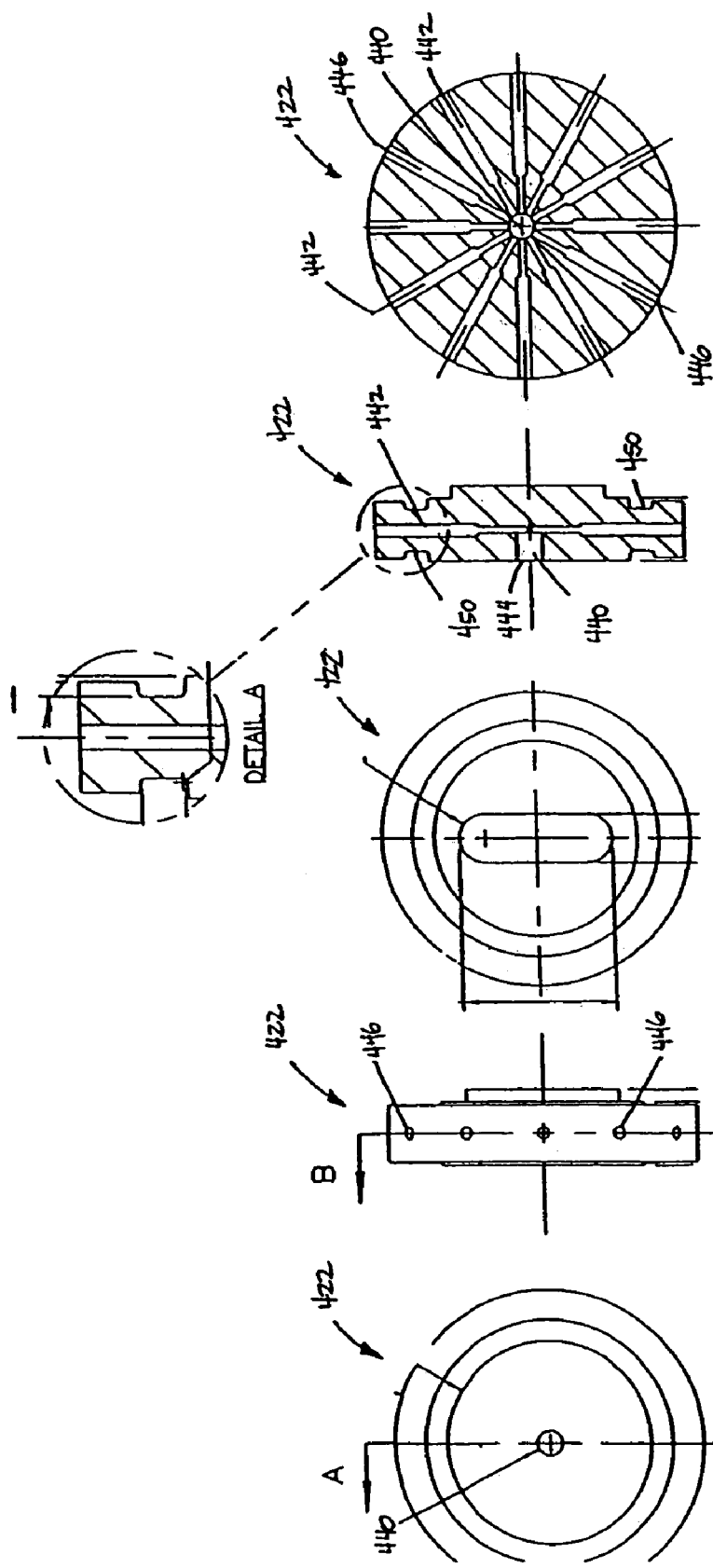

METHODS AND COMPOSITIONS FOR CHROMATOGRAPHY

CROSS-REFERENCE TO RELATED APPLICATIONS

This application is a continuation of U.S. patent application Ser. No. 10/293,916, filed Nov. 12, 2002 now U.S. Pat. No. 6,942,804, which claims the priority of U.S. Provisional Patent Application No. 60/344,745, filed Nov. 9, 2001, each of which is incorporated by reference in its entirety herein.

TECHNICAL FIELD

This application relates to methods and devices for chromatography and composition used therewith.

BACKGROUND OF THE INVENTION

The goal of chromatography is to separate materials. Chromatography techniques are used for a variety of purposes, from research in basic science to purification of pharmaceuticals. The application of chromatography techniques to production levels works to some degree but when methods and devices are scaled up to the large sizes needed for pharmaceutical or biological product production, most methods and devices work inadequately.

There are many different kinds of chromatography methods and materials. Some of these include paper and thin layer chromatography methods, columns and resins of all types, high pressure liquid chromatography, expanded bed techniques, and reverse phase and reverse flow methods. For example, the first stage in many purification processes of proteins from a fermentation broth, whether from microbial, plant, or animal cell culture, is capture of the desired proteins from the broth. A typical method for accomplishing this is to use an adsorbent material in an expanded bed. On a large scale, the expanded bed uses an upward operating flow through the bed and the flow rate is restricted by increased viscosity, the density of chromatographic adsorbents used, and the rate of binding of the desired protein to the adsorbent. There are also only a few adsorbent materials, such as beads, that can be used due to the presence of only a few types of functional binding groups, particle size, and density of the particle. Additionally, the columns used to perform the chromatography often become contaminated by bacterial or fungal growth, or blocked due to cellular debris. All of these problems lead to a slower process with less material isolated.

The majority of processes for producing pharmaceutical or diagnostic products involve the purification of proteins and peptides from bacteria, yeast and plant or animal cell culture fluids, or extracts from tissues. Usually purification plants use multiple unit operations, including a number of chromatographic steps to ensure the removal of impurities and contaminants. The type of product produced and its intended use will dictate the extent of purification needed. Each step in the recovery process will affect the overall process efficiency by increasing operational costs and process time, and by also causing loss in product yield. Careful selection and combination of suitable unit operations during the design phase may reduce the number of steps needed. The fewest possible processing steps offers the most efficient way of reaching high process efficiency and low costs in the overall production process. Most currently used processes still involve multiple steps of processing which add to the costs, loss of product and offer opportunities for contamination.

Problems in isolation of materials begins in the earliest stages, such as clarification of a fermentation broth or an initial tissue homogenization. Standard techniques for removal of cells or debris are centrifugation and microfiltration. The efficiency of a centrifugation step depends on particle size, density difference between the particles and the surrounding liquid, and viscosity of the feedstock. Although microfiltration may yield cell free solutions, the flux of liquid per unit membrane area is often dramatically decreased during the filtration process. Fouling of the microfiltration membranes is another problem that significantly adds to the operational cost. The combined use of centrifugation and filtration often results in long process times or the use of comparatively large units causing significant capital expenditure and recurrent costs for equipment maintenance. It also results in significant product loss due to product degradation. What is needed are methods, compositions, and devices that allow for direct adsorption from crude feed stocks that can reduce the time and cost of the initial steps of purification.

An alternative to methods of clarification and packed bed chromatography is adsorption to a resin in a stirred tank. This technique is often useful when recovering the target substance from a large volume of crude feed. This method has long been used on a commercial scale for the isolation of plasma coagulation Factor IX with DEAE Sephadex. A major drawback to this system is that well-mixed batch adsorption process is a single-stage adsorption procedure and requires more adsorbent to achieve the same degree of adsorption as in a multi-stage (multi-plate) process such as packed bed chromatography.

A very widely used technique for bulk separation is adsorption of the target molecules in a fluidized bed. This technique can eliminate the need for particulate removal. Fluidized beds have been used in industry for many years for the recovery of antibiotics including batch-processing techniques for recovery of streptomycin and semi-continuous systems for novobiocin. In a fluidized bed, channeling, turbulence, and backmixing is extensive, and is similar to a batch process in a stirred tank. The single equilibrium stage in a fluidized bed decreases the efficiency of the adsorption process with low recoveries, causes the need for re-cycling the media, inefficient washing procedures and increased processing time.

Approaches to solving these problems have been tried by many techniques so that a fluidized bed would have separation characteristics similar to packed bed chromatography. One approach uses segmentation of the bed by insertion of a number of plates with suitably sized holes into the adsorption column. In another approach, magnetic adsorbent particles and a magnetic field over the fluidized bed column are used to stabilize the bed. A substantial stabilization of the bed was achieved using magnetic adsorbents but the experiments were carried out at small laboratory scale and scaling up requires complicated and expensive equipment. Another approach uses agarose in a column equipped with a liquid distribution inlet giving a plug flow in the column.

When these expanded beds were actually used with mixtures of proteins and cells there was some improvement. The breakthrough capacity in such beds, expanded by a factor of two, was very similar to the breakthrough capacity in a packed bed. However, low flow velocities had to be applied to prevent the bed from expanding too much, which resulted in a low overall productivity.

Problems also occur with the particles used for separation. Many standardly used particles are not sturdy enough to withstand the weight of a large column bed, nor can they withstand harsh chemical treatments used for cleaning the beds and columns. The packing materials or resins deteriorate over time due to clean-in-place procedures, harsh buffer conditions, and changing buffer conditions. Additionally, the entire column, piping, or resins may become contaminated, either through bacterial or fungal growth, or through accumulation of material on the particles or resins and that lowers the efficiency. This requires expenditures for replacement of the resins, cleaning all equipment and then assurances that the column has been returned to a good, reliable working condition.

Therefore, a need exists for systems, methods and devices that can separate biomaterials or chemicals that overcome the problems seen with currently used chromatography devices. It is preferred that such systems, methods, and devices be capable of using chromatographical techniques and resins or materials to isolate and separate biomaterials are chemicals more efficiently, and with lower production costs.

SUMMARY OF THE INVENTION

The present invention is directed to methods and devices for using compositions for separating and isolating biomaterials, chemicals or other materials. In particular, the present invention comprises devices that can contain particles without the need for support structures. Preferred methods and devices are described in U.S. Pat. Nos. 5,622,819; 5,821,116; 6,133,019; and 6,214,617; and U.S. patent application Ser. Nos. 09/316,566; 09/870,928; 09/773,027; 09/788,991; and 10/153,161; all of which are incorporated herein by reference in their entireties. In general, such devices when used for growth of cells are referred to as "CBR" or centrifugal bioreactor. When applied to the separation and isolation techniques taught herein, the devices are collectively designated as "CCD" or centrifugal chromatography devices.

In general, the devices of the present invention comprise novel apparatuses for containing chromatography materials, such as bed materials, beads, resins or gels which are immobilized within chambers mounted in a centrifugal field while liquids, with or without any gas phase(s) in contact with the liquids, are flowed into and out of the chambers. The bed materials are ordered into a three-dimensional array of particles, the density of which is determined by the particle size, shape, intrinsic density, and by the selection of combinations of controllable parameters such as liquid flow rate and angular velocity of rotation.

In an alternative embodiment, the bed materials are not confined in closed chambers, but rather are immobilized in open chambers formed by and between adjacent disks. As with the other disclosed embodiments of this invention, the inflow of nutrient fluid into the chamber is one force that counterbalances the centrifugal force exerted on the bed materials to immobilize the bed materials in the open chamber. Using a summation of vector forces, a CCD is capable of maintaining particles or a resin in a chamber to form a bed with which materials are separated using chromatography techniques. All standard chromatography techniques, including but not limited to, adsorption, ion exchange, size separation, affinity chromatography, ion exclusion, ligand exchange, reversed phase and normal phase partitioning, are used in the CCD. The chromatography materials used in a CCD include those materials used in chromatography methods, and are not limited by particle fragility due to column weight considerations. Methods also include low, medium and high pressure liquid chromatography. Such methods can be used for analytical, semi-preparative processes, initial clarification, preparative filtration and process scale applications. The chromatography system is easily created in a CCD and thus, dismantling the system for cleaning, if necessary, is also easily accomplished.

In general, the methods comprise addition of a desired chromatography material to the chamber or chambers of one or more CCD and forming a bed or chromatography plates by running the CCD, adding the liquid from which the target molecules are to be separated, and collecting the isolated target molecules.

Accordingly, the present invention comprises methods for isolating materials comprising devices comprising one or more CCDs which use compositions for chromatography.

The present invention may be understood more readily by reference to the following detailed description included herein. Although the present invention has been described with reference to specific details of certain embodiments thereof, it is not intended that such details should be regarded as limitations upon the scope of the invention. The entire text of the references mentioned herein are hereby incorporated in their entireties by reference.

BRIEF DESCRIPTION OF THE DRAWINGS

FIG. 7 is an illustration of a three-dimensional array of particles in a rotating conical biocatalyst immobilization chamber.

FIGS. 18A and 18B show end and cross-sectional views of one side of a chamber according to the embodiment of the invention shown in FIGS. 15 and 16A-B.

FIGS. 19A and 19B show cross-sectional views of one side of the chamber according to the embodiment of the invention shown in FIGS. 15 through 18A-B.

FIGS. 20A and 20B show end and cross-sectional views of another side of a chamber according to the embodiment of the invention shown in FIGS. 15 and 16A-B.

FIGS. 23A-23E show side and cross-sectional views of a manifold sleeve of the CCD according to the embodiment of the invention shown in FIG. 15.

DETAILED DESCRIPTION

Figure 1:
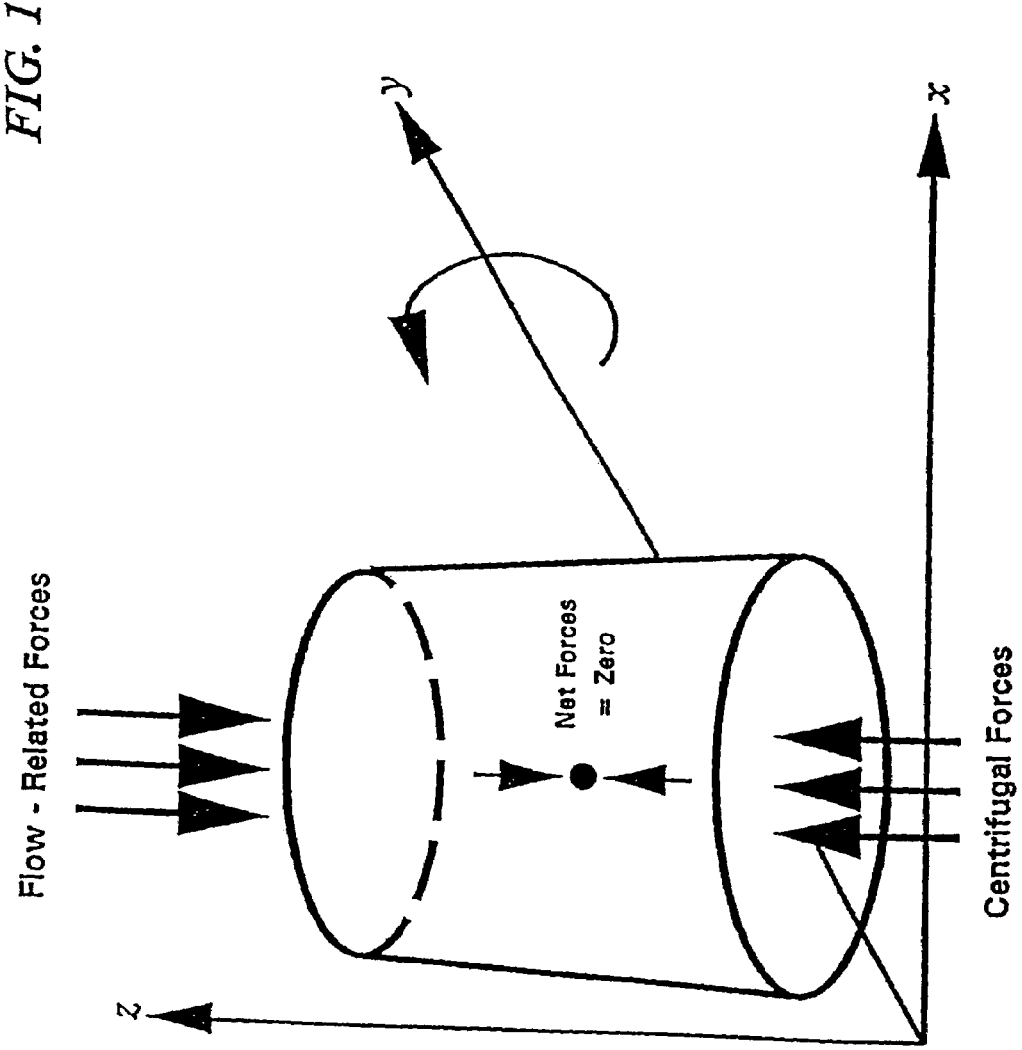
FIG. 1 illustrates the process of an apparatus of this invention.

In general, the present invention is directed to methods for isolating materials using devices described herein and compositions comprising media and particles for chromatography techniques. The invention contemplates the isolation of one or more specific components from a more complex material, such as isolation of proteins or peptides from fermentation broths or tissue extracts, or chemicals from chemical reactions. Any materials that can be isolated by chromatography methods can be isolated by the methods, devices and compositions described herein, and the invention is not limited by the description of specific materials or chromatography techniques.

Methods for isolating target molecules, similar to those currently used for isolating molecules, comprise using one or more of the devices described herein, referred to as CCDs, centrifugal chromatography devices. The present invention includes, but is not limited to, methods of clarification, filtration, single-stage adsorption, batch adsorption absorption methods, ion exclusion chromatography, normal phase partition, reverse phase partition, polar separations, nonpolar separations, hydrophobic separations, hydrophilic separations, ligand exchange, ion-pairing, size exclusion and affinity chromatography methods.

For example, the initial purification step or steps of isolating a target molecule begins by adsorption chromatography using a conventional bed of adsorbent positioned within a CCD. Prior to addition of a starting material, such as a fermentation broth, a tissue extract or a chemical reaction mixture, the starting material is generally clarified or at least, large particulates are removed. Standard techniques for removal of cells or debris are centrifugation and microfiltration. The efficiency of a centrifugation step depends on particle size, density difference between the particles and the surrounding liquid, and viscosity of the feedstock. When handling small cells, such as $E.\ coli$, or cell homogenates, small particle size and high viscosity reduce the amount of material that can be used in each centrifugation and often makes it difficult to obtain a completely particle-free liquid. Centrifugal methods are known to those skilled in the art and such methods can be used prior to adsorption or at any step where concentration of target molecules is needed. Alternatively, centrifugation can be replaced by methods of separation in a CCD. The crude starting material can be added to a CCD used in a preparative step, where for example, a bed of size separation beads are used to hinder the movement of larger materials in the starting material while smaller materials flow through to the next processing step.

To obtain a solution that can be further purified by chromatography, centrifugation is usually combined with filtration methods, such as microfiltration. The methods of the present invention comprise use of CCD with pretreatment or post treatment of the material by centrifugation or filtration steps. Filtration includes filtering methods using membranes and filters made from known materials and comprising pore sizes comprising ranges from nanometer to micron to millimeter to meter sized pores.

A method contemplated in the present invention is adsorption to a resin. This technique is often useful when recovering the target substance from a large volume of crude feed. Methods of single-stage adsorption and batch adsorption are contemplated by the present invention. Resins are added to a CCD and the crude feed, or media to be clarified, or any other liquid is added. The CCD and resin can be used to isolate plasma coagulation factors with DEAE Sephadex.

The CCD and methods of the present invention for single-stage adsorption or batch adsorption are advantageous over standard chromatography methods because the resin or other bed material can be easily added and withdrawn from the CCD, by, for example, changing the rotation speed. Once a batch of liquid has been through the bed, the bed is removed and a new bed of the same type or a different type is added to the CCD and processing can continue. In other methods, a loop system can be used to return the liquid through the bed more than one time to assure complete removal of target molecules from the liquid, or to saturate the bed material. Once the target molecule is removed from the liquid and is adsorbed onto the bed material, the liquid is processed in a CCD or other device downstream. If the bed material has a target molecule adsorbed onto it that is wanted, the bed material is either treated within the CCD to release the bound target molecule, or the bed material can be removed from the CCD and treated to remove the target molecule. If the bound target molecule is not wanted, the bed material can be cleaned within the CCD or removed from the CCD and cleaned or discarded.

A method for bulk separation of target molecules is adsorption of the target molecules in a fluidized bed. In some applications, this method eliminates the steps for particulate removal. Fluidized beds are created in a CCD by establishing a bed material in the CCD by the summation of the vector forces, so the particles of bed material remain suspended in substantially the same location within the CCD and then flowing the media having the target molecules through the bed material.

There are a large number particles that can be used in the methods of the present invention and in the CCDs for separation of target molecules from the media that contains them. For example, agarose support particles have long been used in chromatography methods. Commercially available adsorbents based on amorphous silica have also been used. These adsorbents are denser than agarose-based adsorbents, but the smaller bead size enables this material to expand to the same degree as beds of agarose beads at comparable flow velocities. There is no limitation in the present invention for the type of particles used as the bed material. Any particle that can be used in standard chromatography methods are contemplated for use in the methods and devices of the present invention. Particles that specialized for particular target molecules or for particular media conditions are also contemplated by the present invention.

As used herein, isolation of a target molecule includes all of the steps involved in the process of isolating the target molecule. For example, steps of clarifying or centrifuging stock feed broths is included in isolation of the target molecule, generally as the first step in the process of isolation. The processes may or may not lead to a target molecule that is free of the starting material, but includes any stage of purification that is reached by a particular step or process.

Methods of the present invention comprise preparation or isolation of target molecules by one or more CCDs. The CCDs can be used individually, in serial arrangement or in parallel arrangements, and in combinations with other separation techniques and apparatus. One process step can be performed in one CCD and the eluent from a first CCD can be fed into a second or more CCDs. This system can be used, for example, for a method of treating large amounts of liquid in CCDs, all of which comprise the same bed material, so that all of the liquid is treated at one time by many CCDs, in either a serial pathway or a parallel pathway. Alternatively, a method comprises adding a liquid comprising a target molecule to a first CCD having a particular bed material, having the liquid effected by the conditions in the CCD, and then adding the liquid leaving the first CCD to a second CCD having a different bed material. For example, the crude feed stock is added to a first CCD having a bed material that provides a sizing function and removes larger materials such as cells or cellular debris. The liquid leaving the first CCD, having been acted on by the bed materials, no longer contains as many cells or as much cellular debris as it did prior to being exposed to the bed material. This treated liquid is then fed into a second CCD, that has a bed material that acts as an ionic exchanger.

In these methods, one processing step can be performed on a large amount of starting material, such as stock or broth material, chemical reactions or tissue extracts, or multiple steps of purification or isolation can be performed. Additionally, the starting material can be fed into one CCD in a continuous loop in order to provide multiple passes of the heterogeneous liquid over the isolating or separating material (particles) contained within the chamber or chambers of the CCD. In this way, a particular target molecule can be thoroughly removed from the starting material, which leads to greater amounts of target molecule obtained, or the liquid can be cleared of unwanted materials.

The chromatography materials added to one or more CCDs include all known types of materials used in chromatography techniques, particularly those used in packed bed or expanded bed columns, and low, medium and high performance liquid chromatography columns. The choice of material added to one or more chambers of the CCDs is determined by the starting material, such as tissue extract, chemical reaction mixture or stock broth, any preprocessing steps, and the target molecule or molecules to be isolated. In the methods of the present invention, because the CCD contains the bed materials by a combination of vector forces and does not rely upon either a support structure or the other bed materials to hold the bed materials in place, compression of the bed materials does not occur like that found in conventional column techniques. Therefore, smaller materials or materials not capable of being used at higher pressures can be used in the present invention. The choice of chromatography materials is not limited by the same considerations as those found in conventional chromatography and the present invention contemplates such novel uses of these materials. The present invention also comprises methods and compositions of buffers and eluents that are known to those skilled in the art.

A beneficial aspect of the present invention is that the CCD is easily maintained. In general, the chromatography material, herein referred to as resin, gel, bead, or bed material, is easily added to the chamber or chambers through a port. The bed is formed by, among other forces, rotation of the chamber to the desired speed, to yield the size and shape needed for the particular application. The combination of the vectors of force, including, but not limited to, centrifugal force, the force of the media stream and gravity, allow the particles to form a bed in the interior of the chamber of the CCD wherein each particle is independently suspended in relation to every other particle of resin. This allows for efficient exposure to all surfaces of the particle, no packing of the particles, no back flow pressure problems and the particles are maintained within the chamber, so that there is no contamination of the media exiting the chamber with particles. By changing the forces, including the rotation parameters, the particles can be easily flushed from the chamber if necessary, and the empty chambers can be cleaned or sterilized for another run. The particles can be recharged or cleaned while they are maintained within the chamber or flushed, cleaned and added back to the chamber.

The forces created in the CCD cause the bed within the chamber to form quickly after addition of the particles, which are generally added with liquid. Once the preferred force summation, including rotation parameters, is reached within the CCD, the bed will maintain the desired density and shape. Should processing steps require a different flow speed of the target molecule through the bed, the density and shape of the bed is easily changed by changing the force parameters of the CCD. One CCD has the capability of providing a multitude of different chromatography techniques, even without changing the particle type. For example, a CCD with sizing particles, at a particular force summation parameter, can be used to initially filter a fermentation broth by passing the broth quickly through the bed so that only large materials are retained, by for example, forming a lower density bed and having higher flow media so that only large materials are retained. The particle bed is easily cleaned by washing. The same CCD can then form a more dense particle bed by using different rotation and operating force parameters that allow for longer retention time by the target molecule.

The CCD methods and compositions overcome the problems with packed bed chromatography, while providing excellent separation. The packed bed is a depth filter, and this it is an excellent collection device for particulate matter. The smaller the packing media, the better it acts as a filter. Bonded resin column packing materials are suitable for separating certain solutes, but are also capable of retaining other components of the sample indefinitely. These retained compounds may significantly decrease column efficiency and selectivity. If proper care of the column is not taken then time and money are wasted when the column is ruined in a short time. Column maintenance is a constant expense with attendant labor costs.

The CCD does not accumulate materials due to packing constraints because a change in the force summation parameters can expand the distance between each packing particle so that the each particle can be flushed clean on all surfaces.

Additionally, if the packing materials become contaminated with adhered materials, the packing materials can be easily flushed out of the CCD chamber and new packing material added while the original packing material is cleaned or recharged, or the material may be cleaned or recharged within the chambers. The chambers of CCD can be made from any sturdy material and therefore are resistant to harsh buffers or materials, making them easily cleaned.

Examples are provided herein for applications of the methods and compositions of the present invention. These examples are for illustration and are not to be seen as limiting the invention. The invention comprises separation of molecules using CCD, and any separation techniques that can be adapted to a CCD are contemplated by the present invention. In particular, the invention comprises compositions comprising known particle types and novel applications of particle types that cannot be currently used because of limitations in standard chromatography applications such as columns. Where one CCD or one chamber is described, it understood that multiple CCDs or chambers are also intended. Where particular components are described, it is understood that the individual components, pressure levels, resin or particle types, chamber shapes, liquid, liquid flow and rotation parameters are not limiting to the invention and that novel combinations of these and other components are included in the present invention.

As used herein, particles, beads or resins are used interchangeably and include any particles or materials that can be used for chromatography. A particle is capable of being used for chromatography if it functions in a CCD to form a bed, such as in column chromatography, and acts to separate molecules in the liquid or media that is added to the CCD chamber. The particles forming the bed are formed into a bed and held substantially in one location within the chamber by the summation of the vector forces acting on the particles. Examples of particles include, but are not limited to, agarose, sepharose, silica beads, mixed composition beads, anionic beads, cationic beads, affinity chromatography beads and specialty beads with functional groups. These chromatography materials are known and are commercially available from companies such as BioRad, of California, and Amersham Biosciences, Piscataway, N.J.

The present invention comprises methods and compositions used with a CCD such that the CCD functions as an expanded bed or packed bed chromatography device. The CCD can use adsorbents to form stable fluidized beds at high operating flow velocities. Ion exchange resins are used, such as those made from highly biocompatible agarose base matrix with an inert crystalline quartz core material to provide the required density. The defined particle size and density distribution of the adsorbents yield expanded beds with well-defined and consistent hydrodynamic properties, and with adsorption characteristics similar to those of packed beds of standard chromatography media.

CCD methods with expanded bed characteristics can be used for initial recovery of target proteins from crude feed-stock. The process steps of clarification, concentration and initial purification can be combined into one unit operation, providing increased process economy due to a decreased number of process steps, increased yield, shorter overall process time, reduced labor cost and reduced running cost and capital expenditure. Additionally, all kinds of source materials can be used in processing such different materials including, but not limited to, bacterial homogenate, bacterial lysate, *E. coli* inclusion bodies, products secreted from bacteria, yeast, insect, animal, and plant cells, yeast cell and other cellular homogenates, whole hybridoma fermentation broth, myeloma cell culture, whole animal cell culture broth, milk, animal tissue extracts, plant tissue extracts, unknown source materials, chemical reaction mixtures, metal slurries, and culture supernatant from a continuous fluidized bed bioreactor. Source materials are also referred to as heterogenous liquids. The heterogeneous liquids can be highly heterogeneous, meaning that the liquid contains very many different kinds of molecules, or the heterogeneous liquid may only comprise more than one molecule, such as a liquid taken at a late step in the purification process.

CCD methods and devices can provide a single pass operation in which desired proteins are purified from crude, particulate-containing feed-stock without the need for separate clarification, concentration and initial purification. The CCD bed created by the design of force parameters allows for a distance between the adsorbent particles, providing an increased void volume fraction in the bed, which allows for unhindered passage of cells, cell debris and other particulates during application of crude feed to the column.

Crude, unclarified feed, a highly heterogeneous liquid, is applied to the CCD bed and target molecules are bound to the adsorbent while cell debris, cells, particulates and contaminants pass through unhindered. Any target molecule can be trapped this way and the method can be accomplished using different adsorbant or absorbant materials. Weakly bound material, such as residual cells, cell debris and other type of particulate material, is washed out from the bed using liquid flow. Different parameters are then used to elute the captured target molecules from the bed using suitable buffer conditions. For example, the distance between the particles of the adsorbent material is increased and the buffer condition is changed so that the target molecule is released from the adsorbent material particles and enters the eluent phase. The eluent contains the target molecule, increased in concentration, clarified, partly purified, and ready for further purification if necessary. Thus the present invention comprises a method for concentrating a target molecule from a highly heterogeneous liquid comprising adding an adsorbent material to a CCD chamber, suspending the adsorbent material by the summation of the vector forces acting on the adsorbent material, forming a chromatography bed that adsorbs the target molecule and allows other materials in the heterogenous liquid to pass through the bed, eluting the adsorbed target molecule from the adsorbent material and collecting the eluted target molecule. The adsorbed target molecule can be eluted from the adsorbent material while the adsorbent material is within the chamber or chambers of the CCD or is eluted from the adsorbent material after the adsorbent material is outside the CCD.

CCD methods, devices and compositions comprise ion exclusion chromatography methods and materials. In ion exclusion, mobile ions with like charge cannot penetrate the bead, which carries a fixed charge. Highly charged species are excluded from the intraparticle volume and elute sooner. In normal phase partition, the sample is distributed between the intraparticle (bound) water and a less polar mobile phase. By choosing an appropriate buffer, column or bed selectivity can be fine-tuned for a particular compound. Nonpolar compounds are retained more strongly than polar compounds. In reversed phase partition, the sample molecules are distributed between a polar, usually aqueous, mobile phase and a nonpolar (aromatic) resin backbone. The more hydrophobic molecules elute later than less hydrophobic ones. Ligand exchange and size exclusion can also be used. In size exclusion, molecules too large to penetrate the effective pore structure of the resin are physically excluded from the intraparticle volume. The methods and compositions of the present invention comprise a method for separating molecules, comprising, forming a substantially stationary bed within a chamber of a CCD using compositions comprising particles and media, wherein the composition of particles comprises particles that are suitable for ion exclusion and the composition of media comprise liquids that create an ionic environment in which a target molecule is bound by the particles. Alternatively, the methods comprise compositions of media in which the target molecule is not bound by the particles. In another alternative, the methods comprise compositions of particles having pores that are too small for the target molecule to enter. In another alternative, the methods comprise compositions of particles having pores that are sized so that the target molecule enters, and in such a method, the target molecule elutes from the CCD at a later time than if the target molecule had flowed directly through the bed.

Ion exchange chromatography in a CCD can comprise particles such as UNOsphere S strong cation exchange media, made by BioRad. These particles are hydrophilic, spherical polymeric beads designed for the separation of proteins, nucleic acids, viruses, plasmids and other macromolecules. The beads are provided in 100 mM NaCl in 20% ethanol as a 50% (v/v) slurry. The beads are added to the media stream entering the CCD and the bed, made from the beads, is formed within the CCD. Determining the optimal flow rate and bed size is well within the skill of those skilled in the art and is determined by the target molecule to be isolated or separated. The liquid containing the target molecule is added to the CCD in the appropriate buffering conditions and flowed through until the target molecule is either bound to the beads or excluded from the beads. The target molecule is then eluted directly from the CCD bed if excluded, or the target molecule is eluted from the CCD bed with the appropriately buffered media.

All buffers commonly used for anion or cation exchange chromatography are used with the ion exchange beads and methods of the present invention. A variety of buffers can be used in differing steps, depending on the nature of the target molecule and the heterogeneous liquid in which the target molecule is found. The use of buffering ions that have the same charge as the functional group on the ion exchange beads will produce the best results. For example, phosphate ions with cation exchange beads and Tris with anion exchange beads. Cationic buffers include, but are not limited to, acetic acid, citric acid, HEPES, lactic acid, MES, MOPS, phosphate, PIPES, pivalic acid, TES, and tricine. Anionic buffers include, but are not limited to, bicine, bis-Tris, diethanolamine, diethylamine, L-histidine, imidazole, pyridine, tricine, triethanolamine and Tris. The ion beads can be regenerated by washing with 2-4 bed volumes of 1-2 M NaCl. This washing removes reversibly bound material.

Methods comprising reversed phase and ion-paring on silica require complex eluents for effective separations. These mechanisms work on the principle of modifying the compound to be analyzed until it is compatible with the bed material. Alternatively, the bed material can be modified and the chromatographic conditions are optimized to be compatible with the compound, allowing for isocratic elution and no sample derivatization.

CCD applications contemplate the use of ion exchange methods. Ion exchange chromatography is one of the most widely used techniques for protein purification. Two of the most commonly used ion exchange supports are strong anion and cation exchangers. Strong anion exchangers, with quaternary amine functional groups are used for purifying acidic and neutral proteins and peptides. Strong cation exchangers, with sulfonate functional groups, are used for purifying basic and neutral proteins and peptides. Any type of support material that can be used in the CCD device that can bear these and other ionic functional groups are contemplated by the present invention.

CCD Bed Materials

The type of bed material, resin, bead, all of which are interchangeable terms, that are used in the CCD methods and devices will be determined at least in part by the chemical nature of the target molecules or compounds and the solutions in which the target molecule is found. Certain classes of water insoluble or sparingly water soluble compounds are preferably separated on reversed phase particle beds, while other water soluble compounds such as sugars, alcohols and short chain organic acids are preferably separated on the ion exchange resins. Middle range solubility compounds can be separated with several different methods.

A particular advantage of the CCD methods, devices and compositions is that high resolution chromatography supports, such as smaller diameter beads, resins or gels can be used in addition to those used in conventional columns because of the lack of gravity packing in the CCD. The density of the resin, beads or support materials can be lower than standard column bed materials. The input fluids or stock or fermentation broths, which contain the target molecule in impure form can be more viscous that is practical in standard column separations because the density of the bed in the CCD can be so carefully controlled and fine-tuned by rotation and other force parameters. The higher viscosity capabilities allows for less dilution of starting materials and may also prevent preprocessing steps such as filtration. Fluid flow is limited by the rate of absorption, not by physical bed considerations such a minimum fluidization velocities, leading to shorter loading time.

The CCD methods, compositions and devices can be used to separate any biomaterial or inorganic materials that can separated by chromatographical methods. For example, CCD can be used for the analysis of proteins, carbohydrates, alcohols and organic acids in food and beverages, biochemical, biomedical and biotechnology applications. The parameters for separation will be different for the differing target molecules, the starting material and the degree of purification needed. In currently used chromatography, to achieve the high throughput required in industrial applications of adsorption chromatography, flow velocities must be high throughout the complete purification cycle but without the beads being carried out of the column. The design and operational parameters of the CCD permit efficient flow control without loss of the beads.

A method for isolating a target molecule, comprising, suspending chromatography particles in at least one chamber in a centrifugal force field wherein a continuous flow of a liquid acts to create a force which opposes the centrifugal force filed and wherein a gravitational force contributes to the resultant vector summation of all forces acting on the particles, wherein the forces substantially immobilize the particles by the summation of the vector forces acting on the particles, and forming a chromatography bed, adding a heterogeneous liquid comprising the target molecule, separating the heterogeneous liquid by the actions of the chromatography bed; and retaining the separated portion of the heterogeneous liquid comprising the target molecule. This method comprises using any known chromatography particles, including, but not limited to, chromatography particles that are adsorbent, size exclusion, affinity, absorbent, polar, nonpolar, cationic, anionic, ligand exchange, hydrophobic, hydrophilic, and ion-pairing, and others known to those of skill in the art. The actions of the chromatography bed are from the interaction or noninteraction of the particles with the components of the heterogeneous liquid and buffers that are used during the chromatography run of the CCD. The actions of the chromatography bed are to separate or fractionate the heterogeneous liquid in one or more ways, with the target molecule found in at least one of the fractions.

Particles

The CCD bed material can be of all types of resins or materials for the separation methods of the present invention. Additionally, the CCD can use novel combinations of different beads or novel combinations of functional groups or ligands on the same bead. The particles can be, but are not limited to, very porous, macroporous, slightly porous, nonporous, hydrophilic, hydrophobic, highly charged, slightly charged, no charge, rigid, or swellable. The particles can be, but are not limited to, plastics, methacrylate, strong anion exchangers with high binding capacity, low binding capacity, DEAE weak anion exchange particles, high S strong cation exchange materials, or CM weak cation exchange materials.

A commonly used material is agarose, a material proven to work well for industrial scale chromatography. The macroporous structure of the highly cross-linked agarose matrices combines good binding capacities for large molecules, such as proteins, with high chemical and mechanical stability. High mechanical stability is an important property of a matrix to be used to reduce the effects of attrition when particles are moving freely. Because the design of the CCD allows for considerations different from column chromatography, the agarose beads may be smaller or larger or different in amount of cross-linking from standard beads. These changes or no changes are contemplated for all structural materials in the bed materials. Modified agarose matrices may be less brittle than inorganic material such as some glass or ceramic materials.

Particles made only of organic material have limited density and would need to have very large diameters for conventional chromatography considerations such as high sedimentation velocity required. Such large particle diameters result in long diffusional path lengths, which cause considerable mass transfer resistance, counteracting productivity. Unlike conventional chromatography, CCD devices, methods and compositions can employ these larger organic materials. Additionally, the present invention comprises a composite particle containing an inert core material that is denser than organic materials. Such particles can be designed so that their density is high at a reasonable particle size.

Particle polydispersity in bed material is also contemplated by the present invention. The size and density gradients position the beads at specific locations with the CCD chamber. The smaller, lighter particles move to one position and the larger, heavier particles to a different one. Polydispersity in any characteristic is contemplated by the present invention. Size, density, binding capabilities, exclusion pore sizes, support material differences are a few of the wide variety of combinations of components and factors that are used in CCD methods and devices.

HPLC Applications

The present invention comprises methods and compositions for the CCD that give the CCD the characteristics of high performance liquid chromatography (HPLC). The CCD methods include, among others, ion exclusion, ion exchange, ligand, exchange size exclusion, reversed phase and normal phase partitioning, and affinity. These multiple modes of interaction offer a unique ability to separate compounds. The charge on the resin provides the capability of ion exclusion, while the resin material, such as polystyrene backbone, allows hydrophobic interaction to take place. The extent of the interactions depends on the compounds being analyzed and the degree of selectivity required.

Reversed phase and ion pairing HPLC techniques require complex eluent conditions for effective separations. These methods work on the principle of modifying the compound to be analyzed until it is compatible with the bed. Additionally, with resin-based HPLC-like CCD beds, instead of modifying the compound to be analyzed, the bed material is modified and rotation and other force parameters are optimized to be compatible with the compound structure. Resin-based beds allow for the use of an isocratic HPLC system, simplifying sample preparation methods and require no sample derivatization. This shortens sample preparation time, and reduces total analysis time. Filtration may be the only preprocessing step necessary.

Affinity Chromatography

Affinity chromatography is based on the ability of the particles in the bed to specifically bind the target molecule. For example, purification of monoclonal antibodies is one of the major applications of chromatography and CCD methods and compositions comprise purification of antibodies, including polyclonal and monoclonal antibodies, binding portions, Fc regions and fragments of antibodies, and antibody receptors. Protein A and Protein G containing materials are means to purify various classes of immunoglobulins. For example, particles having Protein A or Protein G are used in a CCD bed and the heterogeneous liquid comprising the target molecules, antibodies, is passed through the bed. The target molecule is bound by the Protein A or G and other materials in the heterogeneous liquid pass through the bed. Other receptor-based bed materials can be used to isolate species or subclasses of antibodies.

An example of CCD methods to isolate particular monoclonals is provided. A first CCD comprising a bed material of DEAE beads with Cibacron blue F3GA dye, a mixed mode anion exchange/dye ligand, is used, which feeds directly into a CHT-1 ceramic hydroxyapatite chromatography bed in a second CCD or conventional column. The DEAE-blue resin is a bifunctional affinity gel containing Cibacron blue F3GA dye covalently attached to DEAE agarose. The dye binds albumin and the DEAE group binds the remaining acidic proteins. This offers an alternative separation to Protein A or G binding separation. The combined dye and DEAE material can bind all IgG subclasses, uses mild elution conditions and provides complete removal of all proteases. Under appropriate conditions, the antibody is eluted and the albumin is retained. The hydroxyapatite step further purifies the antibody. The CHT-I bed is useful when the pI of the antibody is close enough to the pH of albumin to cause problems with ion exchange. In addition, the of CHT-I could allow different idiotypes of the monoclonals to be separated.

Another purification method comprises use of a strong cation exchange material for the bed material. At a pH of 4.5 to 5, albumin is negatively charged and does not bind. The antibody is positively charged at this pH and binds to the bed material. The albumin is flushed out of the CCD chamber and the antibody is retained. A sodium chloride gradient can be used to elute the antibody.

Another purification method comprises use of a weak anion exchanger, such as DEAE 20 weak anion exchange material. Most immunoglobulins have pIs in the 6-8 range, and a pH of 7.5 is used for the DEAE bed. Most immunoglobulins bind under these conditions and elute early in a gradient. There is extensive literature describing weak anion exchange conditions for antibodies, allowing for many applications of those methods to CCD devices and methods. With standard chromatography devices there is a disadvantage in using the weak ion exchanger due to the requirement for large equilibration volumes when changing pH. The CCD can change the distance between bed particles by easily changing the rotation and other force parameters and thus allows for less buffer and time in equilibration.

Methods such as these, especially use of the blue dye affinity material which can differentiate between albumin and other proteins, can be used to separate and purify serum and plasma proteins such as complement, fetoprotein, macroglobulin, thyromedin, gelsolin and albumin. Enzymes can also be purified, including, but not limited to, kinases, dehydrogenases and other nucleotide-dependent enzymes. Enzyme substrate affinity beads are also contemplated by the present invention. Biospecific affinity materials are used in the CCD to specifically select for target molecules.

Another selective binding material for affinity chromatography uses boronate-derivatized bed materials. The boronate-derivatized materials can be made from any material used in making chromatography beads, resins or gels, such as polyacrylamide, and can be used with materials that are not currently used because the CCD bed materials comprise different structural concerns for materials. These boronate-derivatized bed materials are used for highly efficient separation of such low molecular weight compounds as nucleotides, nucleosides, catecholamines and sugars. The boronate-derivatized bed materials have an affinity for adjacent cis hydroxyl group (cis-diols) and can separate closely related species such a AMP and cyclic AMP. Methods include separation of cis-diol containing compounds such as cytosine, uridine and adenosine from one another. All of these compounds are bound but their differing affinities permit separate elution. Size exclusion can also be combined with affinity, by using a bed packing density or bead exclusion parameter to separate small molecules.

Individually designed beads (bed materials) can also be used to specifically select for certain target molecules. Bed materials that allow for immunoglobulin coupling to an agarose or other type of support material are contemplated by the present invention. Immunoglobulins can be attached to activated supports through primary amines or other methods such as periodate oxidation of vicinal hydroxyls of the sugars of the carbohydrates found on the Fc region of IgG. These specific antibodies can be directed to any target molecule and can be used for one step separation methods.

Other chemical materials can be used to purify or separate materials in CCD methods and devices. For example, chelating ion exchange resins can be used to bind metals. An example of such a resin is a support material, such as divinylbenzene copolymers, that contain paired iminiodiacetate ions which act as chelating groups in binding polyvalent metals such as copper, iron and other heavy metals in the presence of monovalent cations such as sodium and potassium. This resin has a very strong attraction for transition metals, even in high concentrated salt solutions. Use of such bed materials in CCD allows for environmental clean-up methods in addition to purification of such metals or removal of such metals from biomaterials containing other target molecules.

The methods of the present invention comprise use of apparatus that substantially immobilizes the particles that form the bed by use of the summation of the vector forces acting on each particle. Embodiments of such apparatus have been disclosed in U.S. Pat. Nos. 5,622,819; 5,821,116; 6,133,019; and 6,214,617; and U.S. patent application Ser. Nos. 09/316,566, 09/773,027, 09/788,991, and 10/153,161, each of which is incorporated by reference in its entirety. Though other apparatus have been used for centrifugal immobilization of particles, such as U.S. Pat. No. 4,939,087, they have been unsuccessful at long-term immobilization of particles, cells, biocatalysts, and chromatographic materials because the effect of gravity is ignored. Though microorganisms or animal cells are quite light in weight, their mass is non-zero. Consequently, gravity has a significant effect on the particle, and this effect will increase with time. Over longer time periods, the weight of the suspended particles causes these particles to settle to the lowest regions of the biocatalyst immobilization chamber, disrupting the balance of forces which initially suspended them in the chamber. Further, the aggregation of these particles into a larger particle with virtually the same density as the individual particles results in an increased centrifugal effect which causes the aggregates to migrate to longer radii, eventually clogging the liquid input port.

The apparatus used in the methods of the present invention take advantage of the relationships inherent in (1) Stoke's Law and the theory of counterflow centrifugation; (2) the geometrical relationships of flow velocity and centrifugal field strength; (3) Henry's Law of Gases; and, (4) the effect of hydraulic pressure on media and particles. The methods of the present invention comprise apparatus that are capable of forming chromatography beds by the immobilization of three-dimensional arrays of particles, such as known chromatographic beads and resins.

The theoretical basis of the process utilized by the apparatus of the present invention utilizes a novel method to immobilize particle arrays. A proper application of Stoke's Law in combination with provision for the effect of gravity which also acts on the immobilized particles results in a mathematical relationship which allows for the relative immobilization of such particles. The effect of gravity can be compensated for by an alternative choice of rotational axis as is shown in FIG. 1. If rotation about the horizontal axis (y) is chosen instead of rotation about the vertical axis (z), as is most common in biological centrifugations, then the effect of gravity on immobilized particles will always be limited to action solely in the x-z plane. Since this is the same plane in which both the centrifugal as well as the liquid flow related forces are constrained to act, the motion of a restrained particle at any point in a rotational cycle is the resultant of the sum of the three types of forces acting upon it.

Figure 2:
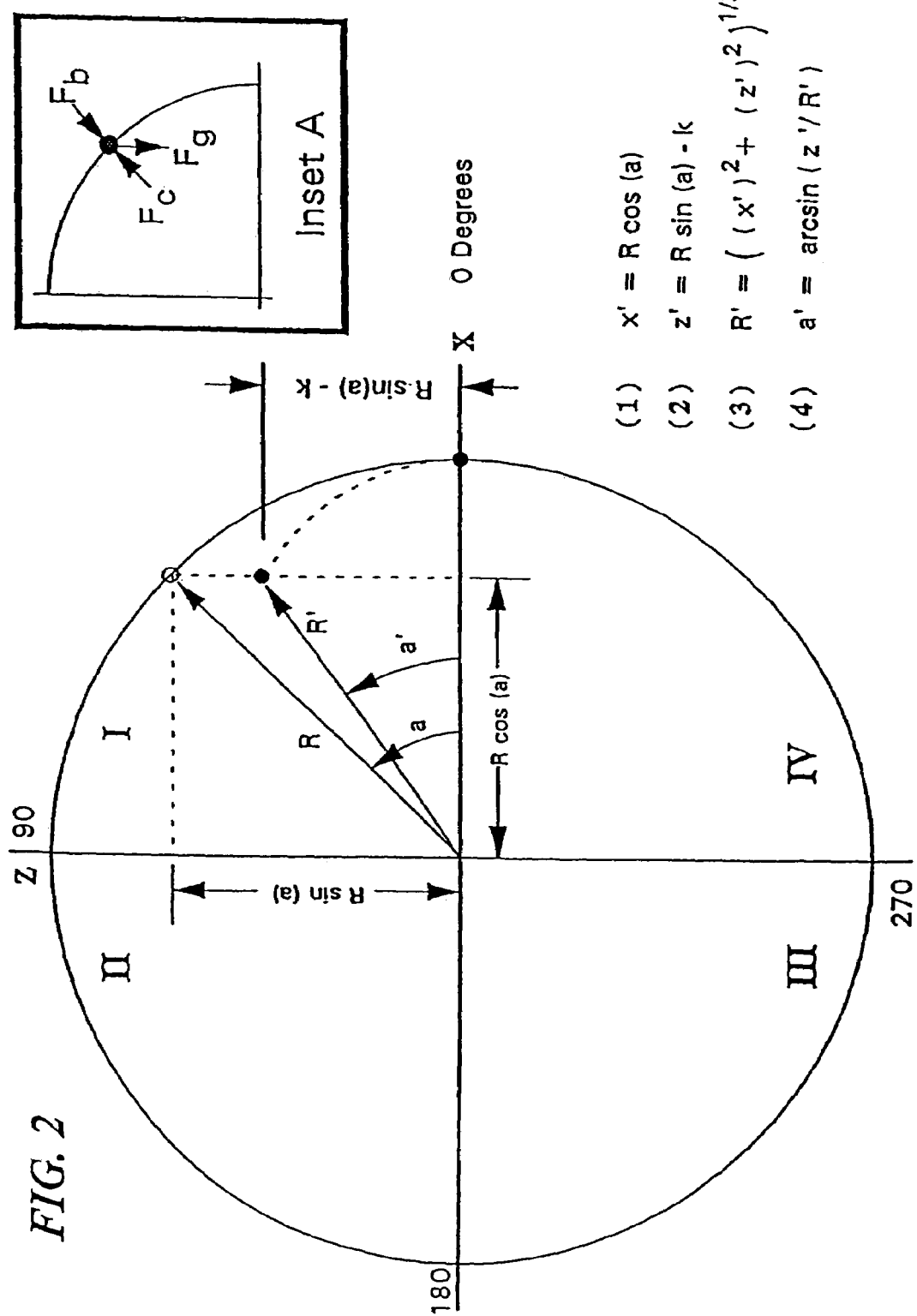
FIG. 2 is an illustration of the mathematics governing the motion of a particle due to the effect of gravity on that particle when it is restrained in a centrifugal field that is opposed by a liquid flow.

As is shown in Inset A of FIG. 2, where the plane of the Figure is the x-z plane, the effect of gravity (Fg) on the position of a particle suspended in a radially-directed centrifugal field (Fc) while an exactly equal and opposing force supplied by an inwardly-directed flowing liquid (Fb) is directed toward the particle, can be calculated by the evaluation of equations 1-4 where (k) represents the downward displacement in the x-z plane imparted by gravitational forces during an angular rotation of the rotor position equal to (a). Analysis of the motion of a particle under these constraints and for $[2\Box \times (k/a)] < R$ (a low mass particle) results in the determination that the motion is periodic; that is, the particle motion results in a return to its starting place after a complete rotation of 360 degrees (after equilibrium is reached). As is shown in FIG. 2, the effect of gravity on the motion of a particle otherwise immobile as a result of the opposing equality of the centrifugal and flow-related forces results in a decrease in radial position in quadrants I and II, and an exactly equal radial lengthening in quadrants III and IV. Thus, the radial distance of the particle from the axis of rotation also exhibits a periodic motion over the course of a full rotation of 360 degrees. It should be noted that, mathematically, measurement of the periodicity of motion requires only one rotation if measurement begins at either 90 or 180 degrees whereas two full rotations are required if measurement begins at either zero or 180 degrees, since a new equilibrium radial distance different from the original results in the latter case.

Figure 3:
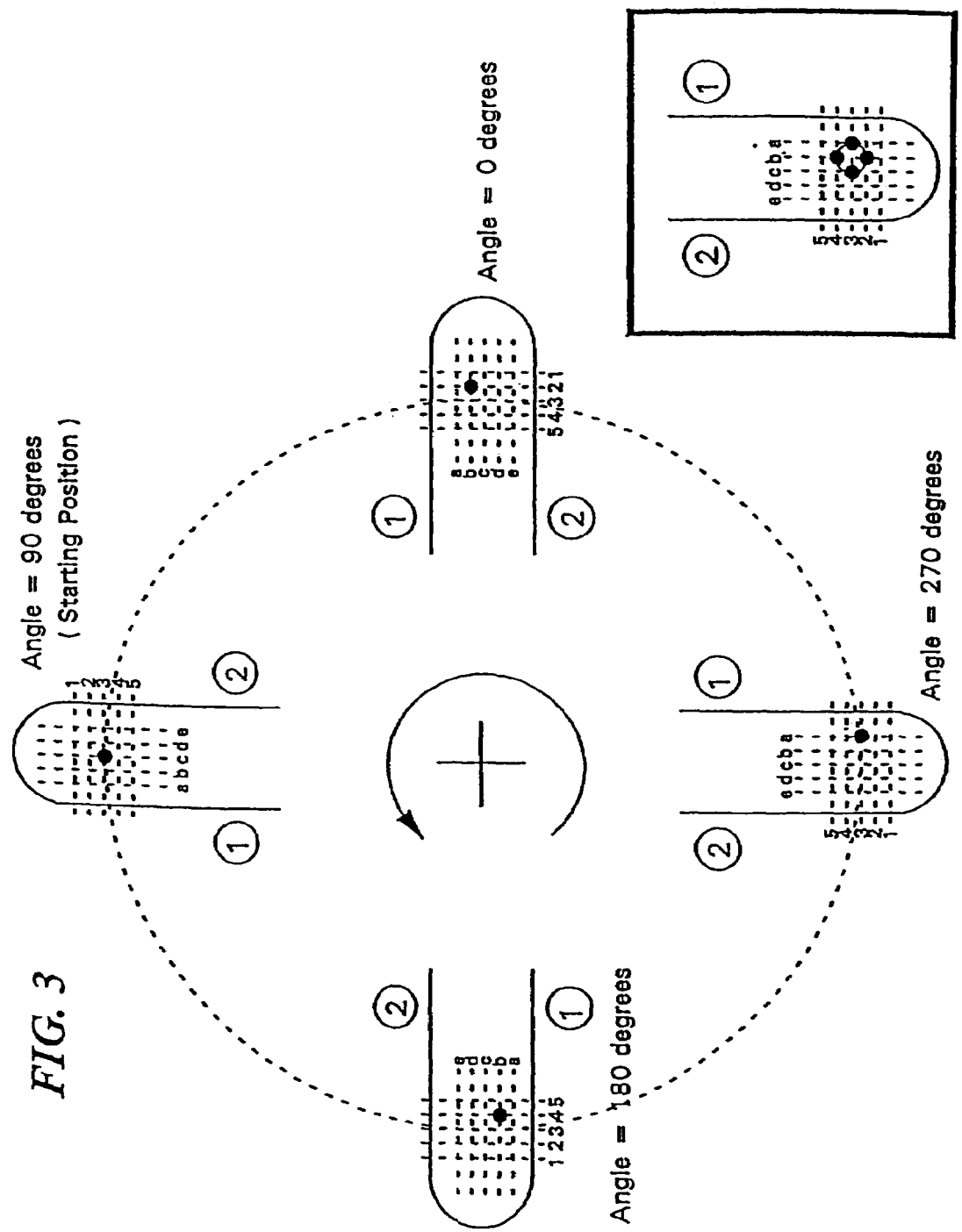
FIG. 3 is an illustration of the resultant motion of a particle under the constraints of FIG. 2.

The effective motion of a particle through a complete rotational cycle is shown in the inset of FIG. 3. If the sides of a container in which the particle is suspended are labeled 1 and 2, then the motion of the particle over the course of one rotational cycle would describe a circle with its center displaced toward the "leading edge" side of the particle's container. Thus, a particle suspended in a centrifugal field which is opposed by an equal liquid flow field will be constrained to periodic motion (and thus is effectively immobilized) if the balance of the radially-directed forces can be maintained over the course of its movement.

Figure 4:
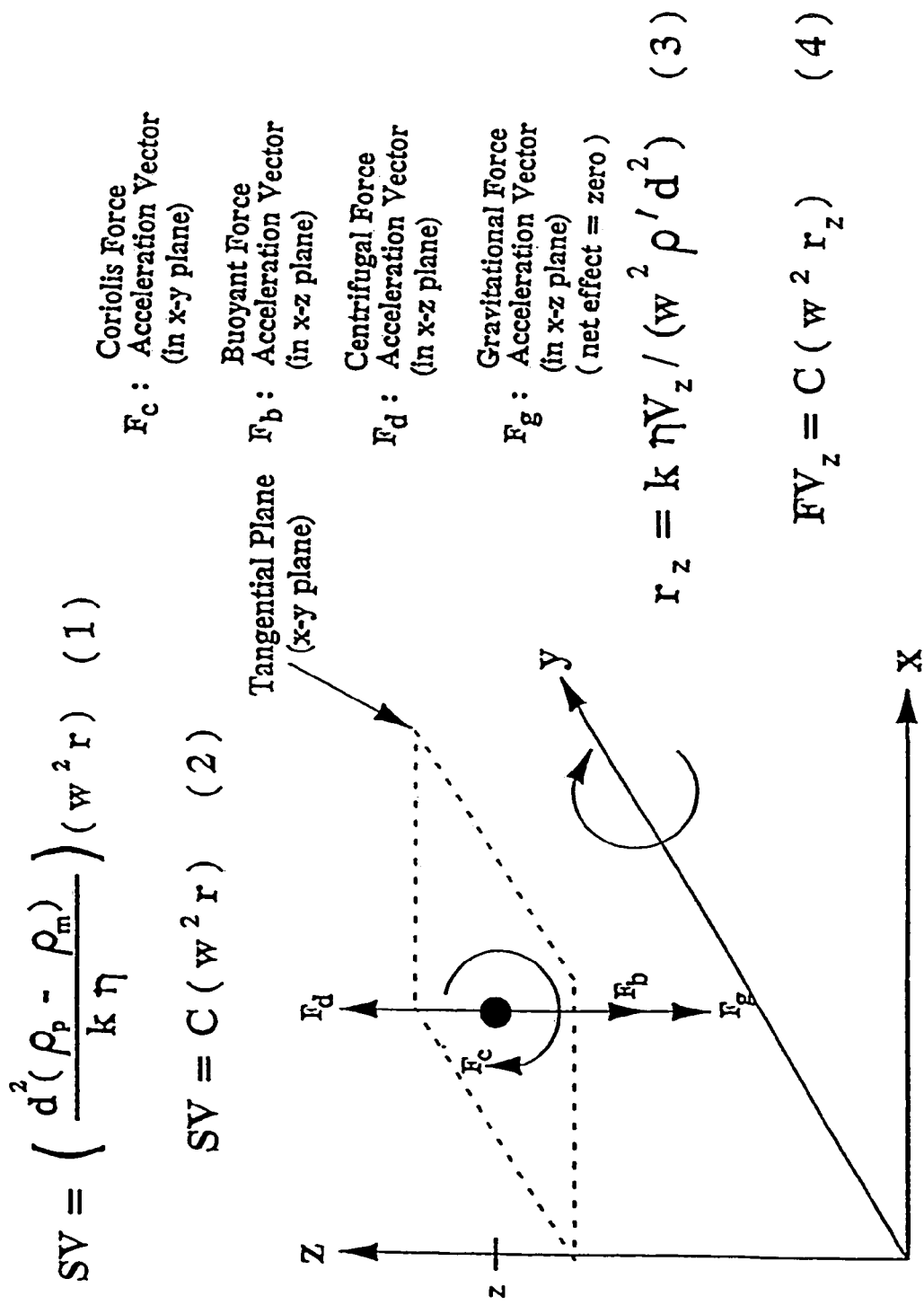
FIG. 4 is a mathematical evaluation of the immobilization conditions at a given radius.

A graphical representation is shown in FIG. 4, in which the axis of rotation is now the (y) axis. Under these conditions the hypothesis of Sanderson and Bird can now be restated and applied to long-term immobilization of particles. There is a radial distance along the z axis (rz) which, when evaluated by Eqn. 3, represents a position in which the particle is relatively immobilized in a centrifugal field which is exactly opposed by an inwardly-directed liquid flow, even in the presence of a gravitational field. Furthermore, a simplification of Stoke's Law (Eqn. 1) under the conditions of uniform particle size, shape, and density and a homogeneous liquid flow results in Eqn. 2, where it is obvious that the Sedimentation Velocity of a particle (SV) is a simple linear function of the applied centrifugal field. Similarly, Eqn. 3 can then be rewritten under the same conditions to yield Eqn. 4, where liquid Velocity (V in Eqn. 3) has been replaced by liquid Flow Velocity (FV). Equation 4 suggests that there is a continuum of liquid flow velocities and applied centrifugal fields which could be matched by the evaluation of constant (C), all of which would satisfy the requirement of relative particle immobilization. Further, if the liquid flow velocity could be varied as a function of (z), there could be a separate application of this equation at each radial distance. Consideration of the implications of Eqn. 4 is important for the relative immobilization of three-dimensional arrays of particles as opposed to the immobilization of two-dimensional arrays of particles at a single radial distance from the rotational axis.

Figure 5:
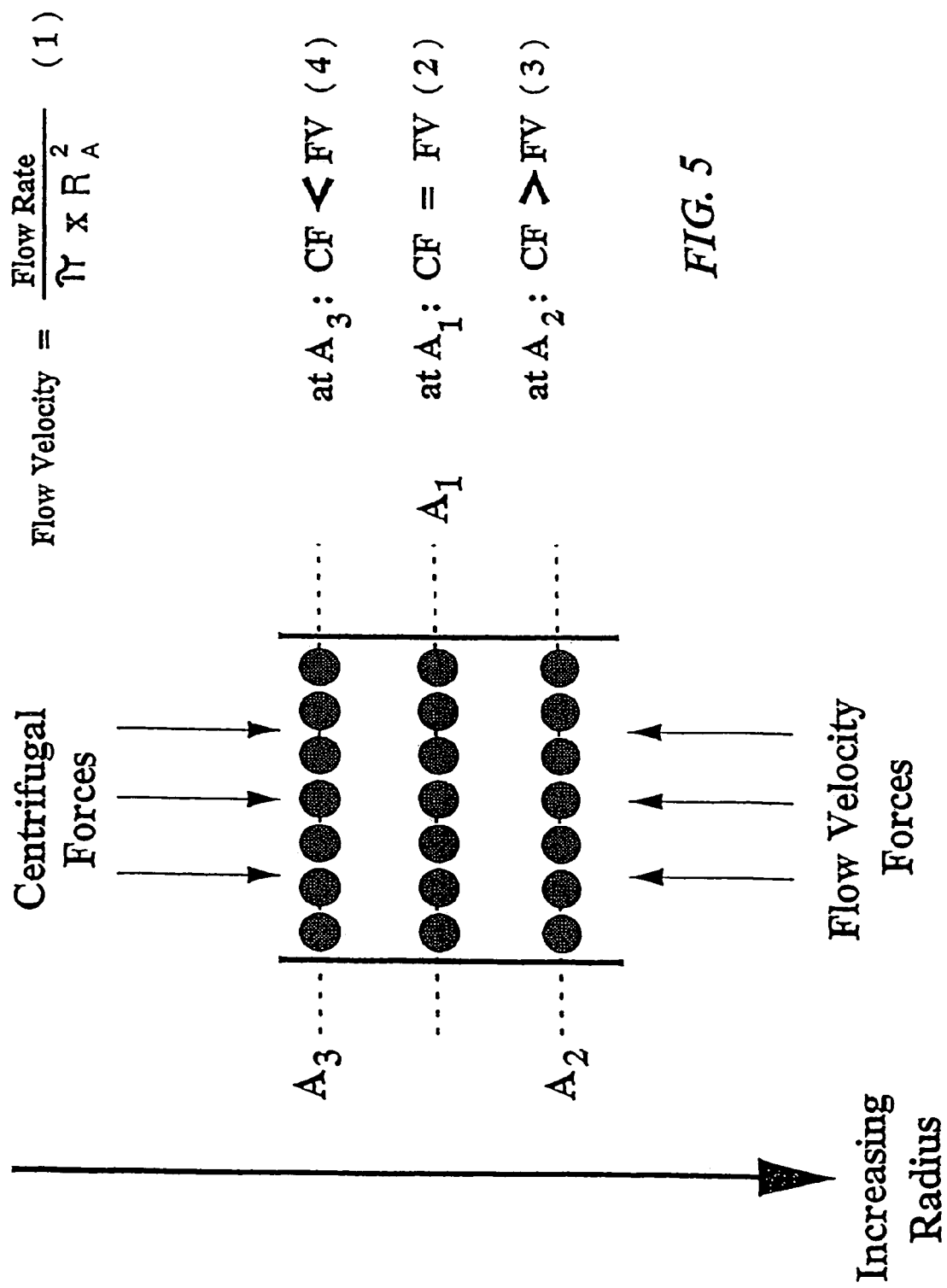
FIG. 5 is an analysis of the balance of centrifugal forces and flow velocity forces in a rotating cylindrical bioreactor chamber.

If the chamber in which a particle is located is cylindrical (as is graphically depicted in FIG. 5) and if a liquid is flowed into this chamber from the end of the chamber most distal to the axis of rotation, then it is obvious that the flow velocity of this liquid flow (as defined in Eqn. 1, FIG. 5) will have a single value at all points not occupied by layers of particles. As a consequence, if a two-dimensional array of particles is in positional equilibrium at a particular radial distance (A1), as is indicated in Eqn. 2, (where CF is the centrifugal field strength and FV is the liquid flow velocity) then particles forced to occupy positions at radial distances either greater than or smaller than A1, such as those located in FIG. 5 at A2 or A3, will necessarily be presented with an inequality of restraining forces which will result in net translation of the particles. Thus, those particles located at A2, a longer radial distance than A1, will experience a greater centrifugal force than those at A1 and will necessarily migrate to longer radial distances (Eqn. 3). Conversely, particles initially located at A3 would experience a reduced centrifugal field and would migrate to shorter radial distances (Eqn. 4). Thus, it is not possible to form a three-dimensional array of particles in a parallel-walled chamber such as that of FIG. 5.

Figure 6:
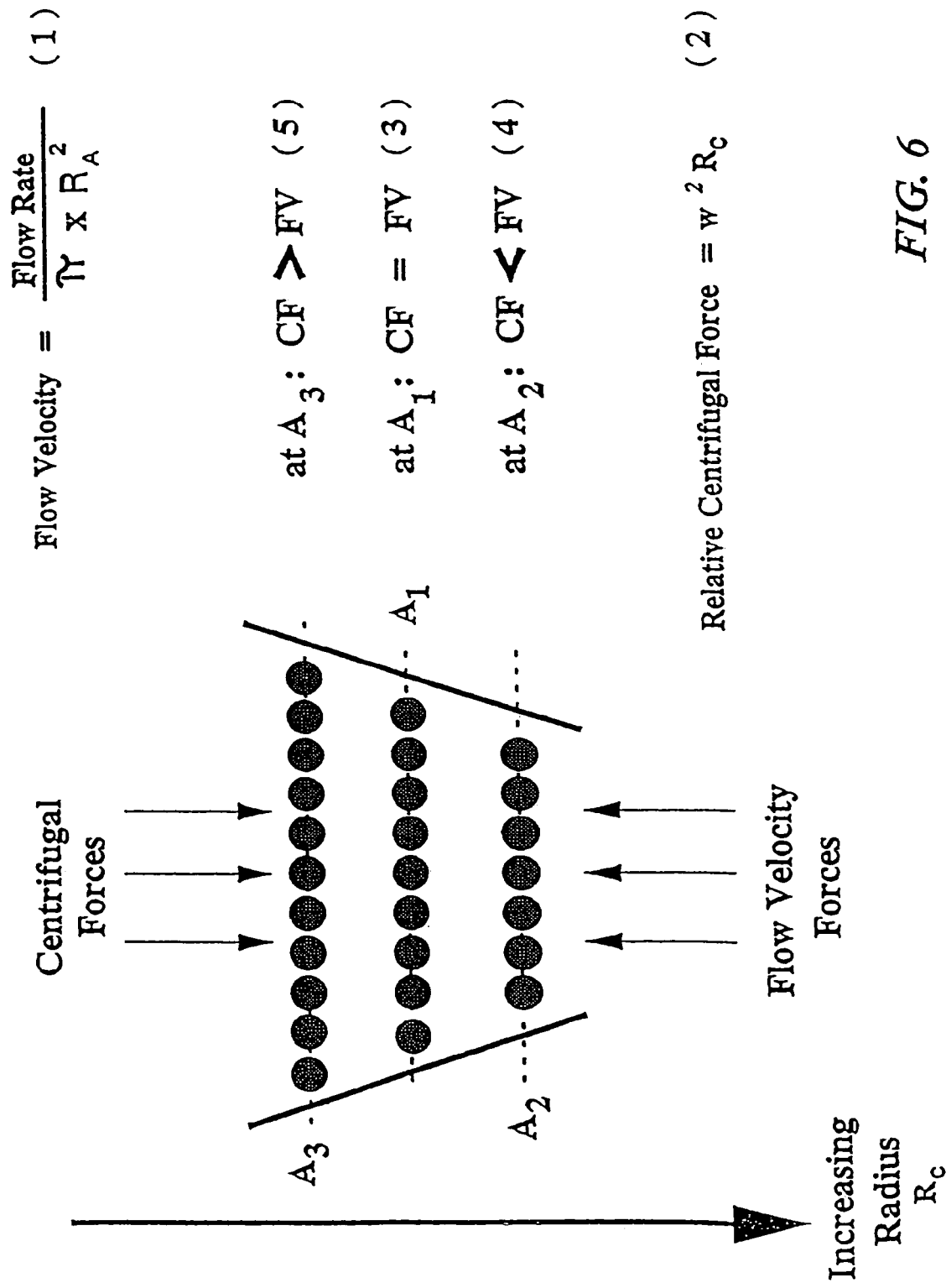
FIG. 6 is an analysis of the balance of centrifugal forces and flow velocity forces in a rotating conical biocatalyst immobilization chamber.

If, however, the biocatalyst immobilization chamber has a geometry such that its cross-sectional area increases as the rotational radius decreases, as is graphically displayed in FIG. 6, then it is mathematically possible to form three-dimensional arrays of immobilized particles. This is a consequence of the fact that the microscopic flow velocity of the liquid flow varies inversely as the cross-sectional area (Eqn. 1) while the relative centrifugal field varies directly as the rotational radius (Eqn. 2). Thus, if values of flow velocity and rotation velocity are chosen such that a two-dimensional array of particles is immobilized at rotational radius A1 (Eqn. 3), then it is mathematically possible to adjust the "aspect ratio" of the side walls of the biocatalyst immobilization chamber such that those particles initially located at radial distance A2 could also experience either an similar equality of forces or, as is shown in Eqn. 4, an inequality of forces which results in net motion back toward the center of the chamber. A similar argument may be applied to particles located at A3 (see Eqn. 5). Although the geometry of the biocatalyst immobilization chamber as depicted in FIG. 6 is that of a truncated cone, note that other geometries could be alternatively used—subject to the constraint that the cross-sectional area of the chamber increases as the rotational radius decreases. Thus, as is depicted in FIG. 7, it is possible to construct a three-dimensional array of particles in a varying centrifugal field opposed by a liquid flow field if the biocatalyst immobilization chamber geometry chosen allows for a flow velocity decrease greater than or equal to the centrifugal field strength decrease as the rotational radius decreases. In the geometry chosen in FIG. 7, that of a truncated cone, the two-dimensional arrays of particles at each rotational radius (Rc) will each be constrained to motion toward that radius where the opposing forces are exactly equal.

Figure 8:
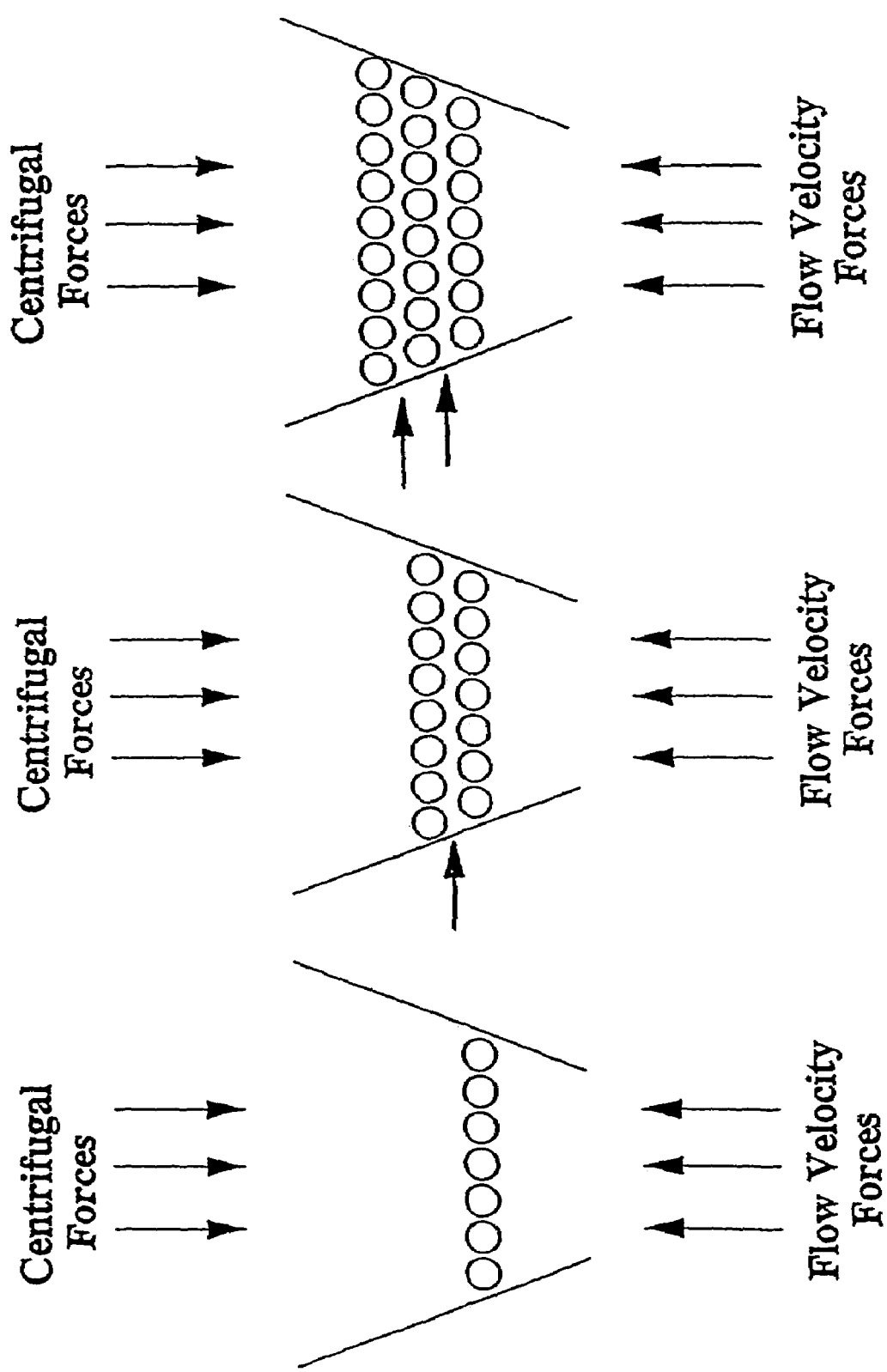
FIG. 8 is an illustration of the inter-stratum buffer regions in a three-dimensional array of particles in a rotating conical biocatalyst immobilization chamber.
Figure 9:
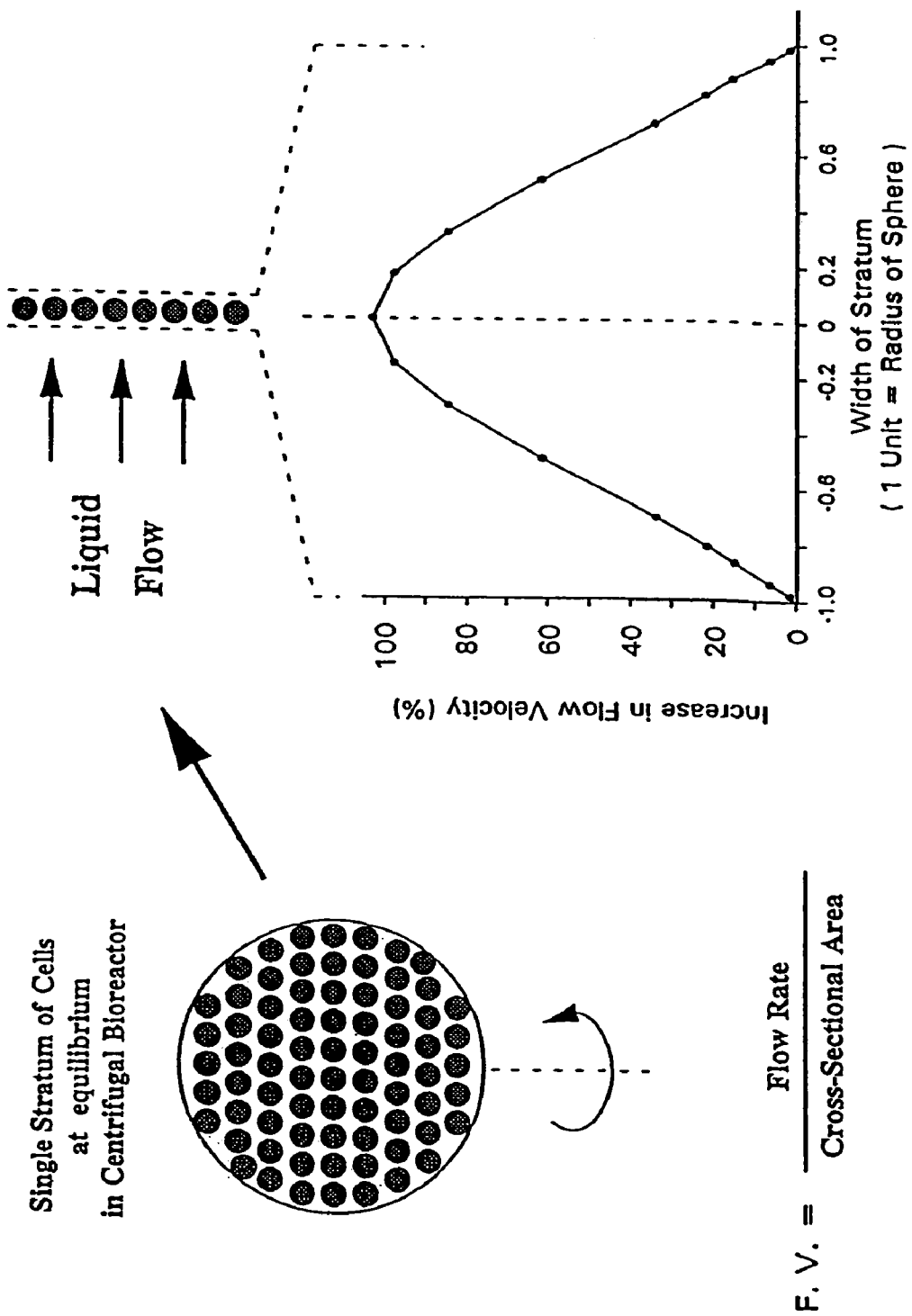
FIG. 9 is a mathematical analysis of the intra-stratum flow velocity variation in a two-dimensional array of particles in a rotating conical biocatalyst immobilization chamber.

While, at first glance, the description presented above would suggest that the net effect of the mismatch of forces at all radii other than that which provides immobilization would result in a "cramming" of all particles into a narrow zone centered on the appropriate radius, such is not the case. As is shown graphically in FIG. 8, as each layer of particles approaches an adjacent layer, it will move into a region where a "cushioning effect" will keep each layer apart (the horizontal arrows in FIG. 8). The explanation for the inability of adjacent layers of particles to interdigitate is a consequence of an analysis of the microscopic flow velocity profile through each layer. In FIG. 9, a single representative stratum of spherical particles confined to a particular radial distance in a chamber layer of circular cross-section is presented. The ratio of the diameters of the particles to the diameter of the cross-section of FIG. 9 is 12:1. While the magnitude of the flow velocity of the liquid through unoccupied portions of the chamber cross-section can be quantified simply from the chamber dimensions at that point, the flow velocity through a region occupied by a stratum of particles will necessarily be much greater than that in the absence of a stratum of particles because of the greatly reduced cross-sectional area through which the liquid must travel. As is shown in the graph in FIG. 9, the increase in flow velocity through a stratum of the above dimensions is more than double that determined in the free space just adjacent to the stratum on each side. This microscopic increase in local flow velocity in the region of each stratum effectively provides a "cushion" which keeps each adjacent stratum separate.

Figure 10:
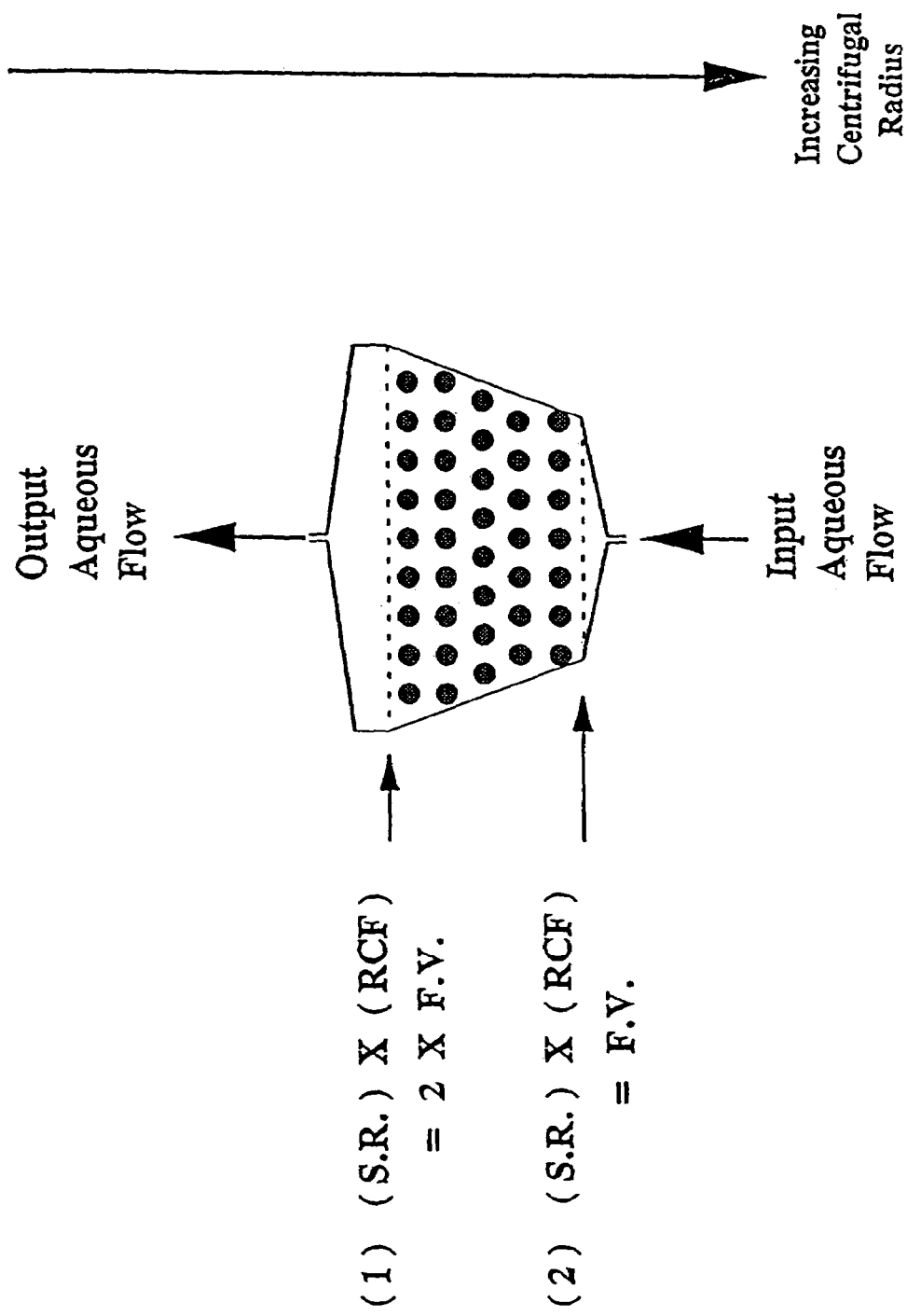
FIG. 10 is an illustration of an example a conical-shaped immobilization chamber and the boundary conditions which determine those dimensions.

In actual use, it has been determined that, for the case of a chamber geometry of a truncated cone, it is preferable that the most distal region of the truncated cone be the region where an exact equality of centrifugal forces and liquid flow velocity is achieved. The "aspect ratio" (the ratio of the small radius of the truncated cone to the large radius of the truncated cone) of the truncated cone is determined by the simultaneous solution of the two equations presented in FIG. 10. In Eqn. 2, the desired boundary condition of immobility for that "lowest" stratum of particles is presented. It states that the intrinsic sedimentation rate of the particle due to gravity (SR) times the relative centrifugal field applied at that radial distance (RCF) be exactly equal to the magnitude of the liquid flow velocity (FV) at that point. In Eqn. 1, a desired boundary condition at the opposite surface of the array of particles is presented. In order to insure retention of all particles within the biocatalyst immobilization chamber, a boundary condition wherein the product of SR and RCF is twice the magnitude of the flow velocity at that radial distance has been arbitrarily chosen. Simultaneous solution of the desired boundary condition equations is used to solve for the ratio of the conic section diameters when the upper diameter and conic length is known.

Figure 11:
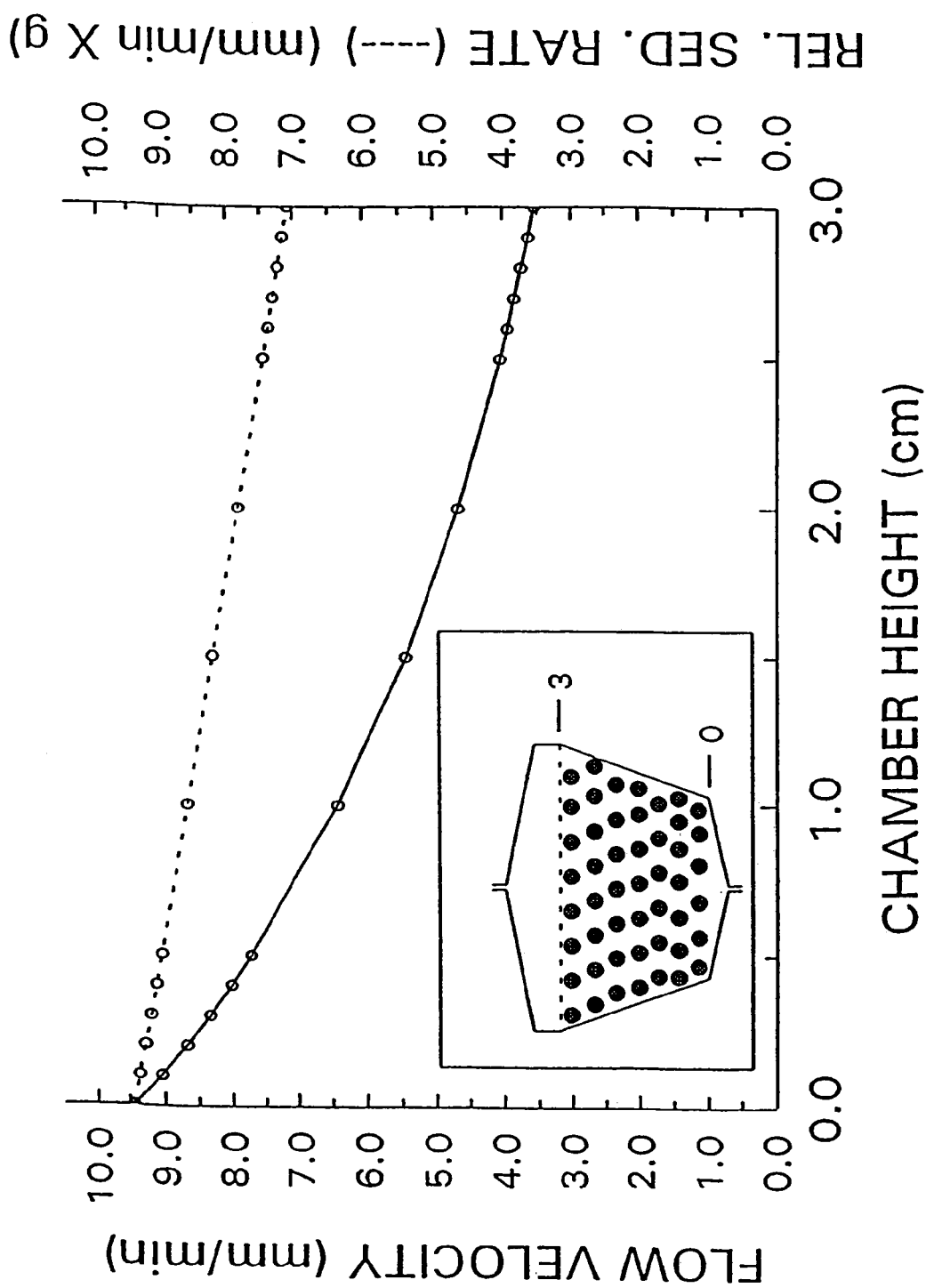
FIG. 11 is an analysis of the positional variation of the centrifugal and flow velocity forces in the chamber of FIG. 10 at a flow rate of 10 mL/min.
Figure 12:
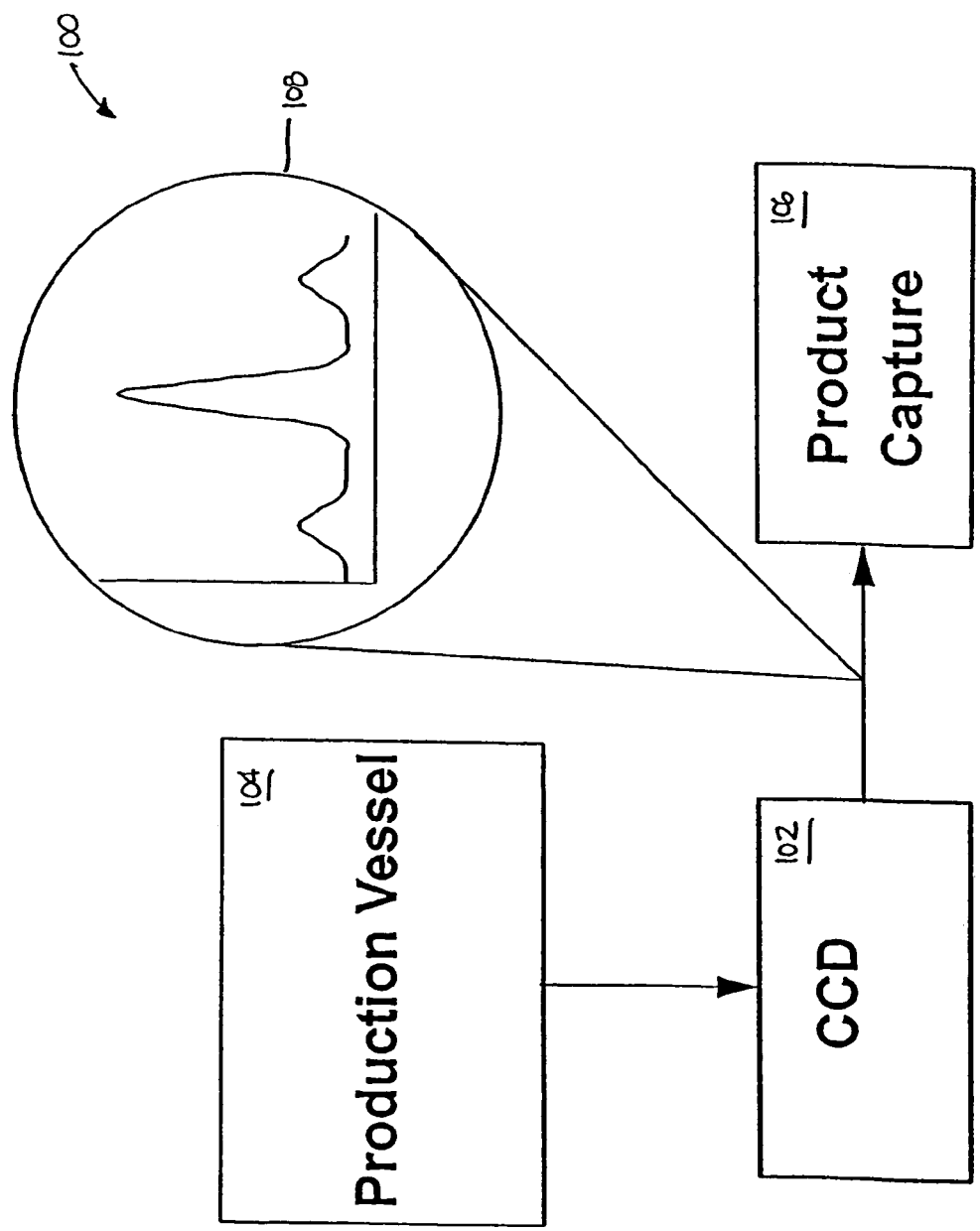
FIG. 12 illustrates a system according to various embodiments of the invention.

FIG. 11 is a profile of the relative magnitudes of the flow-related forces and the centrifugal forces across a biocatalyst immobilization chamber of conical cross-section which has dimensions in this example of: large diameter=6.0 cm, small diameter=3.67 cm, and depth=3.0 cm. We define the Relative Sedimentation Rate as the product of the intrinsic sedimentation rate of a particle due to gravity in a nutrient media at its optimal temperature and the applied centrifugal field. For a given flow rate (in this example 10 mL/min) into a biocatalyst immobilization chamber of the indicated dimensions, where the proximal end of the biocatalyst immobilization chamber is 9.0 cm from the rotational axis, the product of the intrinsic particle sedimentation rate due to gravity and the angular velocity is a constant at the given flow rate in order to satisfy the desired boundary conditions (see FIG. 10). In other words, the angular velocity need not be specified here since its value depends only on the particular particle type to be immobilized. The dotted line in FIG. 11 displays the linear variation in the centrifugal field strength from the bottom to the top of the biocatalyst immobilization chamber, while the solid line displays the corresponding value of the flow velocity. At the bottom of the chamber (the most distal portion of the chamber), the forces are equal and a particle at this position would experience no net force. At the top of the chamber, a particle would experience a flow-related force which is only one-half of the magnitude of the centrifugal field and would thus be unlikely to exit the chamber, even in the presence of a nearby region of decreasing cross-sectional area (the chamber liquid exit port), where flow velocities will increase markedly.

It should be clear from the foregoing that, subject to the necessary condition that the cross-sectional area increases as rotational radius decreases, there are other geometrical chamber configurations whose shape could be manipulated in order to establish boundary and intermediate relationships between the applied centrifugal field and the liquid flow velocity forces at any radial distance in order to establish desired resultant force relationships in the three-dimensional particle arrays. In practice, however, it is undesirable to utilize geometries with rectangular cross-sections as a result of the anomalous effects of coriolis forces which act in a plane transverse to the rotational plane. In the case of rectangular cross-sections, these otherwise unimportant forces can contribute to interlayer particle motion.

It should also be clear from the foregoing that the effect of gravitational forces acting on the individual particle masses which acts independently of the applied centrifugal forces are even less important than was indicated earlier. In particular, since the basic effect of gravity on an otherwise immobilized particle is to either cause radial lengthening or radial shortening, such a motion of a particle will necessarily bring it either into a region of increased flow velocity magnitude (longer radii) or decreased flow velocity magnitude (shorter radii) with only a much smaller change in centrifugal field strength.

As a consequence, the periodic motion of a particle due to gravitational effects on its intrinsic mass will be severely dampened in the presence of such unbalanced opposing force fields and will amount to, in the case of low mass particles, a vibration in place.

It is preferred to control either the introduction of, or the generation of, gases within the immobilization chamber. One may ensure this condition by the application of Henry's Law, which, in essence, states that the quantity of a gas which may be dissolved in a liquid is a function of the system pressure. Thus, if the hydraulic pressure of the liquid-containing parts of the system, including chamber and the liquid lines leading to and from the chamber, are maintained at a hydraulic pressure sufficient to fully dissolve the necessary quantity of input gas and to insure the solubility of any produced gases, then there will be no disturbance of the immobilization dynamics.

FIG. 12 illustrates a system according to various embodiments of the invention. In a system 100 utilizing methods and compositions for separating and isolating target molecules, such as in chromatography, a CCD 102 operates in conjunction with a production vessel 104 and a means for product capture 106.

Typically, a CCD 102 operates independent of an immobilized particle size or particle function. That is, a CCD 102 can be operated at particular liquid flow rate and revolutions per minute (RPM) combinations where arrays of, for example, either 5 or 200 μm diameter ion exchange resin beads or gel exclusion beads are immobilized; and (2) the backpressure or the resistance to liquid flow through an array of immobilized particles is a small fraction of the backpressure of an equivalent packed bed of the same number of particles.

A production vessel 104 can be a conventional device associated with known methods and systems for producing, storing, or otherwise providing a starting material, or heterogeneous liquid, to a chromatographic device such as a CCD 102.

A means for product capture 106 can be a conventional device associated with known methods and systems for capturing, storing, or otherwise receiving one or more products from a chromatographic device such as a CCD 102.

As shown in FIG. 12, a CCD 102 receives the starting material, heterogeneous liquid, produced in a production vessel 104. The CCD 102 captures or otherwise isolates target molecules from the starting material using an appropriate or suitable chromatographic technique. The CCD 102 then provides the target molecules to the means for product capture 106. As shown in 108 of FIG. 12, depending upon the chromatographic technique used by the CCD 102, the CCD 102 isolates target molecules from other materials in the heterogeneous liquid, shown in the inset chromatogram, where peaks indicate the separation of different materials in the heterogeneous liquid.

Figure 13:
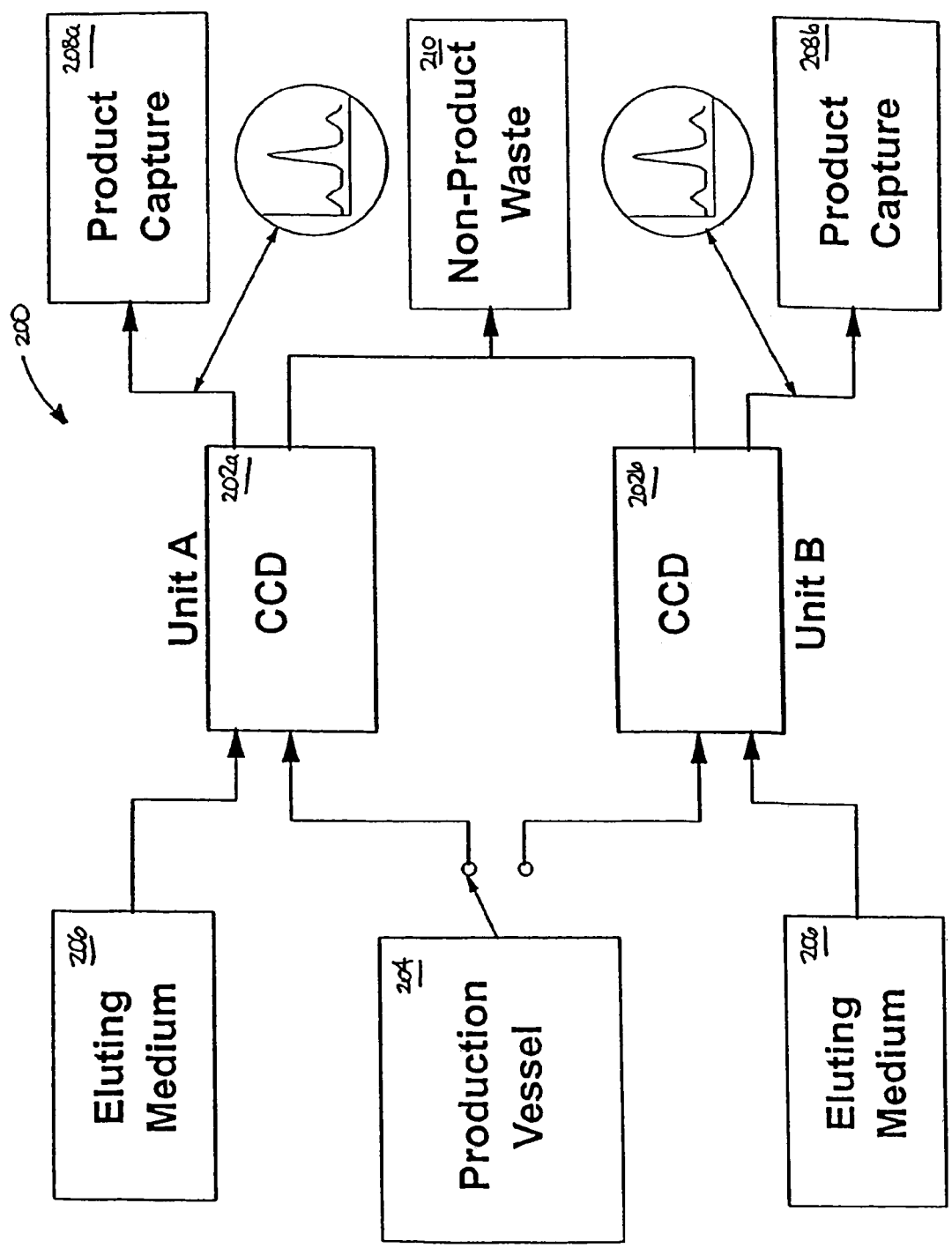
FIG. 13 illustrates another system according to various embodiments of the invention.

FIG. 13 illustrates another system 200 utilizing methods and compositions for separating and isolating target molecules, such as in chromatography, in accordance with various embodiments of the invention. In this embodiment, one or more CCDs 202a,b can be used in respective chromatographic processes to obtain desired product molecules. Each CCD 202a,b includes an immobilized chromatographic particle array, chromatographic bed, in accordance with a chromatographic process. The first CCD 202a can be used as a primary process device, and the second CCD 202b can be used as a backup or overflow process device. Starting material, heterogeneous liquid, from a common production vessel 204 can be pumped to a first CCD 202a and then to a second CCD 202b. An eluting medium 206 such as a liquid of a chemical composition designed to cause the elution of the target molecules from an immobilized chromatographic particle array, can be provided to each CCD 202a,b as needed. Typically, when the fluid flow from the first CCD 202a reaches a particular capacity, subsequent fluid flow is diverted to the second CCD 202b. Respective product capture reservoirs 208a,b connect to each CCD 202a,b to collect target molecules from the chromatographic processes implemented by the CCDs 202a,b. A non-product waste 210, such as a liquid, is output from each CCD 202a,b as a result of the chromatographic processes. Typically, a collection device or storage reservoir captures the non-product waste 210.

For example, the continuous flow-type system 200 can be used in conjunction with classical ion exchange-type or affinity-type chromatography processes. Using these types of processes in conjunction with the CCDs shown in the continuous-flow system 200, target molecules can be obtained from a heterogeneous liquid.

A continuous flow-type process implemented by the system 200 is described below. Initially, a starting material, heterogenous liquid, containing target molecules is introduced such as being pumped from a production vessel 204, to a first CCD 202a. The target molecules are initially adsorbed by the first CCD 202a in a chromatographic particle array made from resin particles. The target molecules become immobilized within the first CCD 202a. When all available binding sites are saturated, an eluting medium 206 subsequently elutes the desired product molecules from the support. Waste liquid from the first CCD 202a is then diverted to a waste reservoir or to non-product waste 210. In this manner, a more purified and concentrated product may be continuously extracted from the production vessel 204.

When the first CCD 202a is about to reach a predefined target molecule binding capacity, the flow from the production vessel 204 is diverted to flow through a second CCD 202b. Output of target molecules from the first CCD 202a can then be diverted to product capture 208a where a target molecule is collected, as shown by the peak in a chromatogram. Output of target molecules from the second CCD 202b can be diverted to a second product capture means 208b. Thus, when the target molecule binding capacity reaches a predefined amount for either the first CCD 202a or second CCD 202b, flow can be diverted to the other CCD as needed. In this manner, the first CCD 202a and the second CCD 202b can be operated in alternating periods to provide a continuous flow of desired product molecules.

Figure 14:
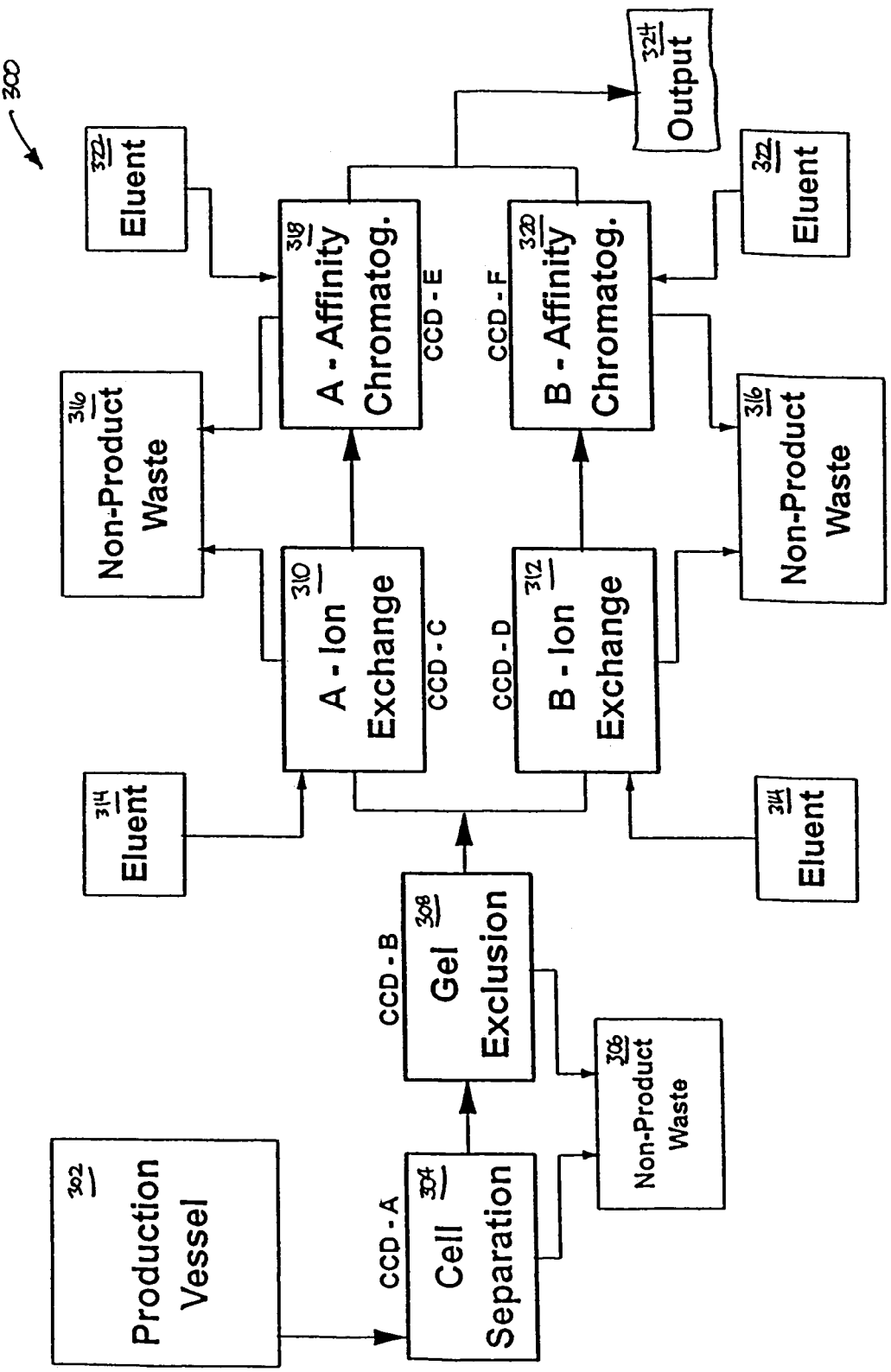
FIG. 14 illustrates yet another system according to various embodiments of the invention.

FIG. 14 illustrates another system 300 utilizing methods and compositions for separating and isolating target molecules, using chromatography, in accordance with various embodiments of the invention. In this embodiment, one or more CCDs are used in a continuous process flow-type scheme in which high molecular weight product molecules can be isolated and purified from a heterogeneous liquid. Similar to the system 200 in FIG. 13, the system 300 provides a heterogeneous liquid from a production vessel 302 to a first CCD 304. In the first CCD 304, the cellular portion of the heterogeneous liquid is removed. Waste is diverted to a reservoir such as non-product waste 306. Next, the cell-free liquid is passed from the first CCD 304 to a second CCD 308, where low molecular weight protein contaminants are discarded and the liquid containing target molecules is passed to downstream purification sections. Waste from the second CCD 308 is diverted to another reservoir or to non-product waste 306. Next, a third CCD 310 and fourth CCD 312 are operated alternatively to first absorb and then elute a more purified and concentrated protein target molecule. Eluent 314 may be added to each of the third CCD 310 and/or fourth CCD 312 as needed. Waste from each of the third CCD 310 and fourth CCD 312 is diverted to separate or common reservoirs such non-product waste 316. A fifth CCD 318 and sixth CCD 320 are employed in alternative operation to adsorb and elute the protein product from affinity chromatography resin arrays. Eluent 322 may be added to each of the fifth CCD 318 and/or sixth CCD 320 as needed. Waste from each of the fifth CCD 318 and sixth CCD 320 is diverted to separate or common reservoirs such non-product waste 316. The resultant product stream is an output 324 in which the protein target molecule has undergone at least four sequential chromatographic purification steps.

FIGS. 15-24 illustrate views of a device or apparatus according to an embodiment of the invention, also generally known as a Centrifugal Chromatography Device or "CCD." The embodiment shown is directed to an apparatus for substantially separating and isolating target molecules, such as in chromatography. Depending upon the type of target molecule to be separated and isolated, and the role of the CCD in a particular chromatographic process, various chromatography resin arrays can be utilized with a CCD.

Figure 15:
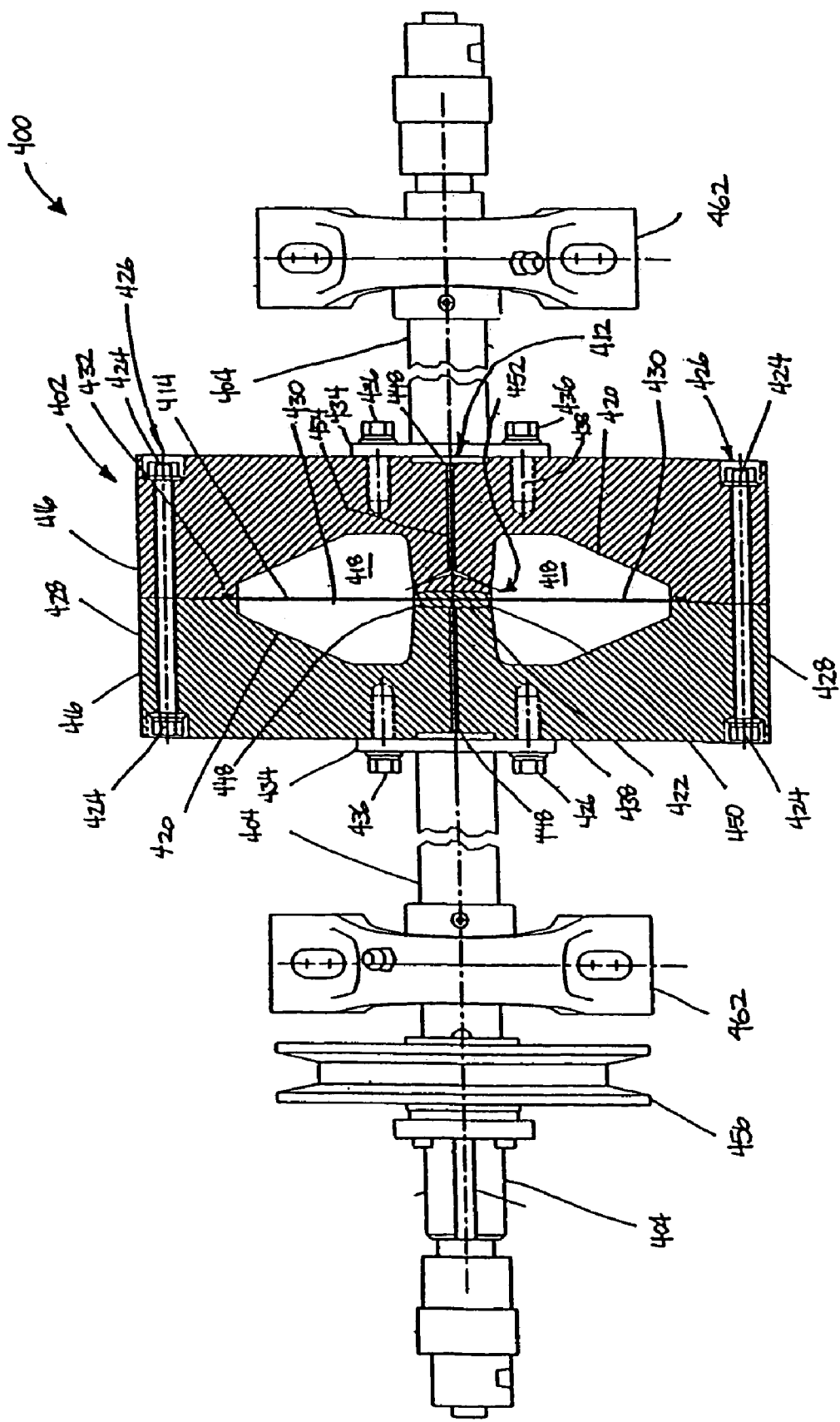
FIG. 15 is a front or side view of a CCD according various embodiments of the invention.
Figure 21B:
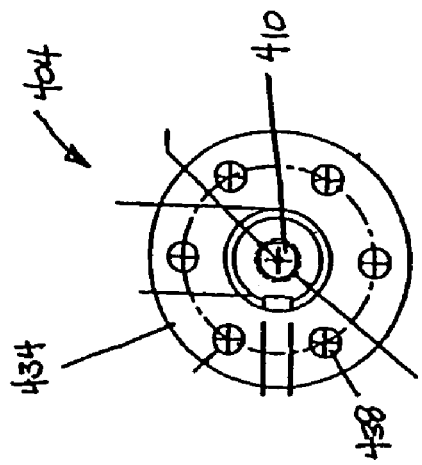
FIGS. 21A and 21B show side and end views of a portion of a shaft of the CCD according to the embodiment of the invention shown in FIG. 15.
Figure 21A:
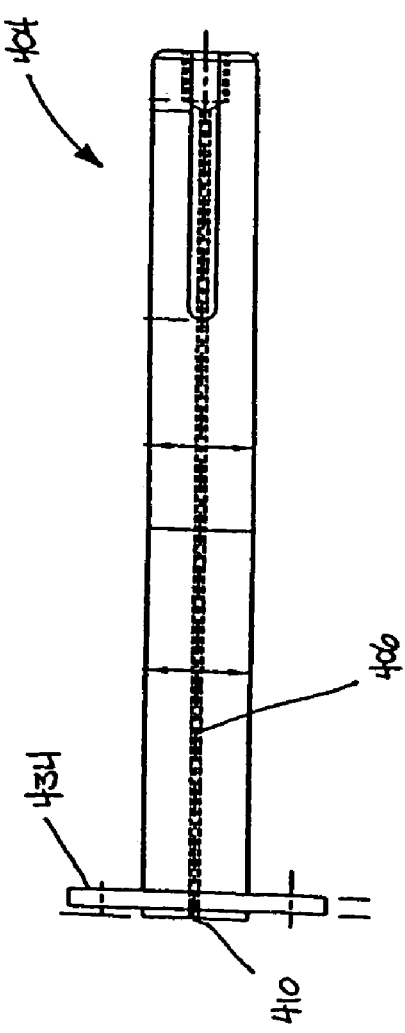
Figure 22B:
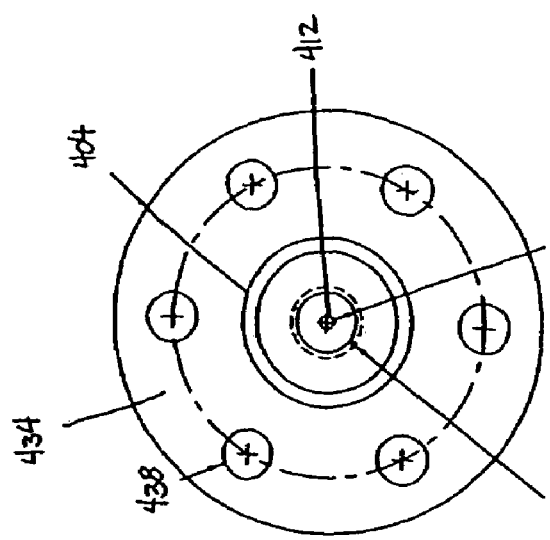
FIGS. 22A and 22B show side and end views of another portion of the shaft of the CCD according to the embodiment of the invention shown in FIG. 15.
Figure 22A:
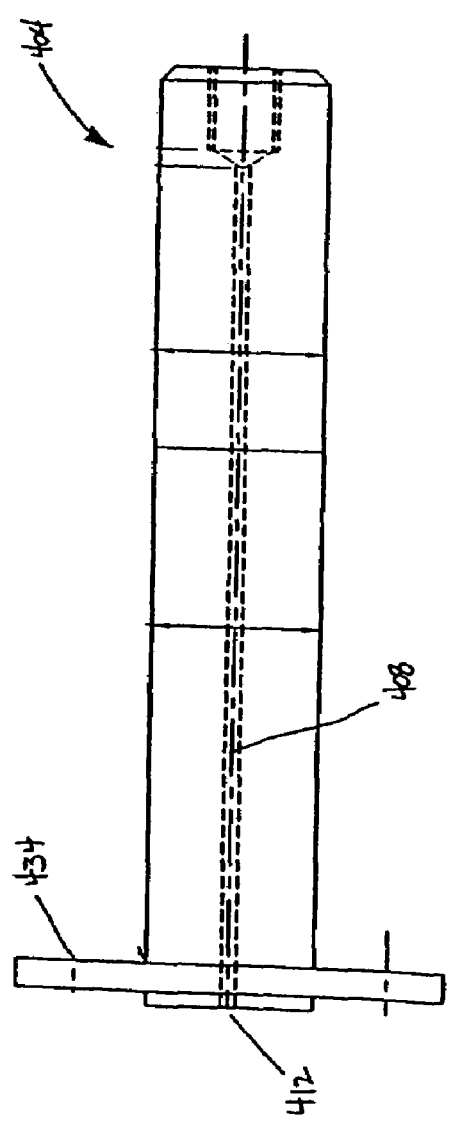

FIG. 15 illustrates a front view of a CCD 400 with at least one chamber 402 for separating and isolating at least one biomaterial. In this embodiment, the CCD 400 includes at least one chamber 402 positioned along a longitudinal axis of a shaft 404. Note that the CCD 400 may include any number of chambers 402 mounted to the shaft 404. Turning to FIGS. 21A and 22A, the shaft 404 typically has an input cavity 406, an output cavity 408, an injection orifice 410, and an output orifice 412. The shaft 404 is typically composed of a stainless steel, typically 304 or 316 stainless steel annealed, ground and polished. However, the shaft 404 may be composed of metals including, but not limited to, steel, iron, and titanium, plastics, composites, combinations thereof, or any material capable of withstanding stresses developed in the CCD 400 during operation.

Figures 16A, 16B:
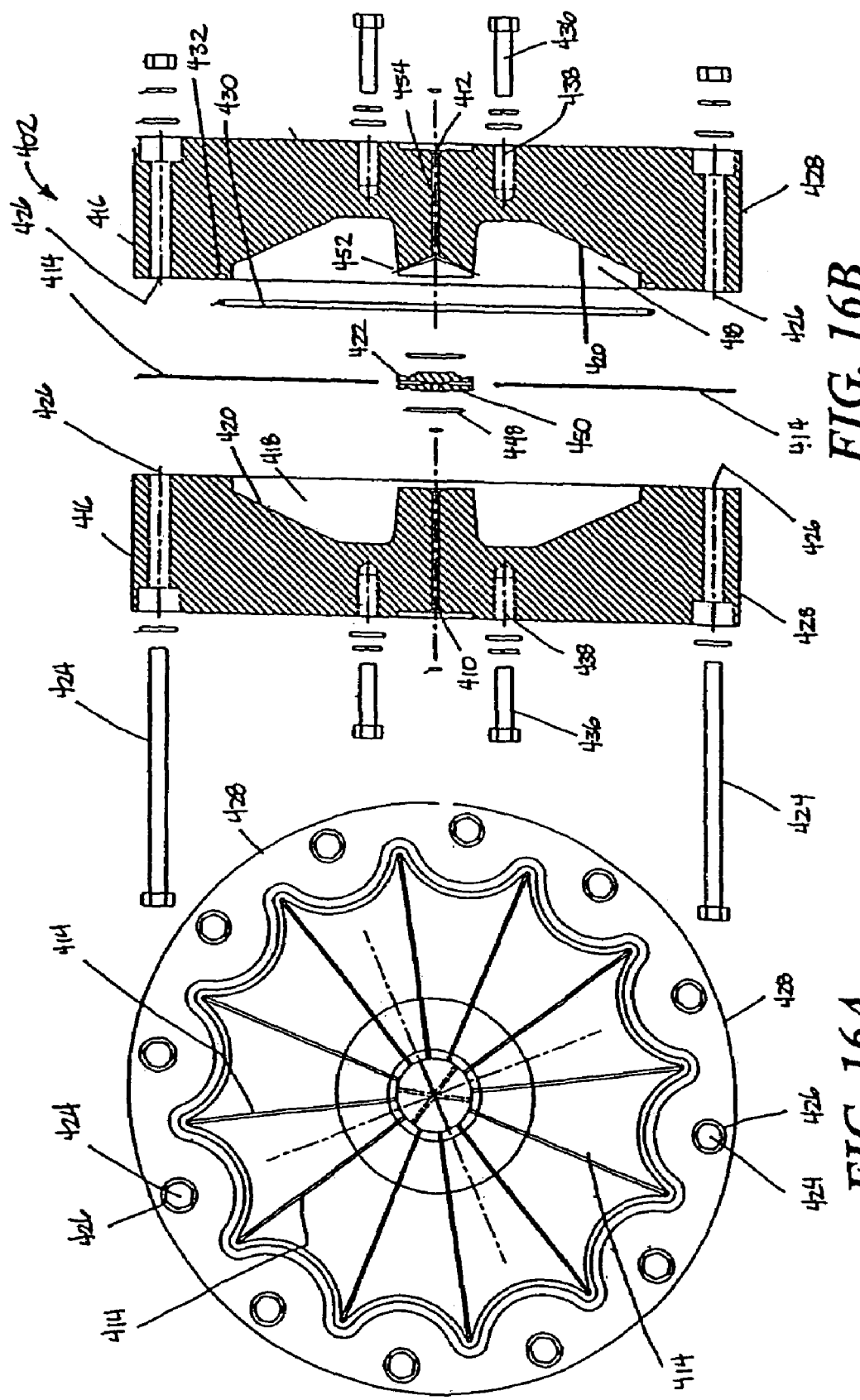
FIGS. 16A and 16B show end and side views of a chamber of the CCD according to the embodiment of the invention shown in FIG. 15.
Figure 17B:
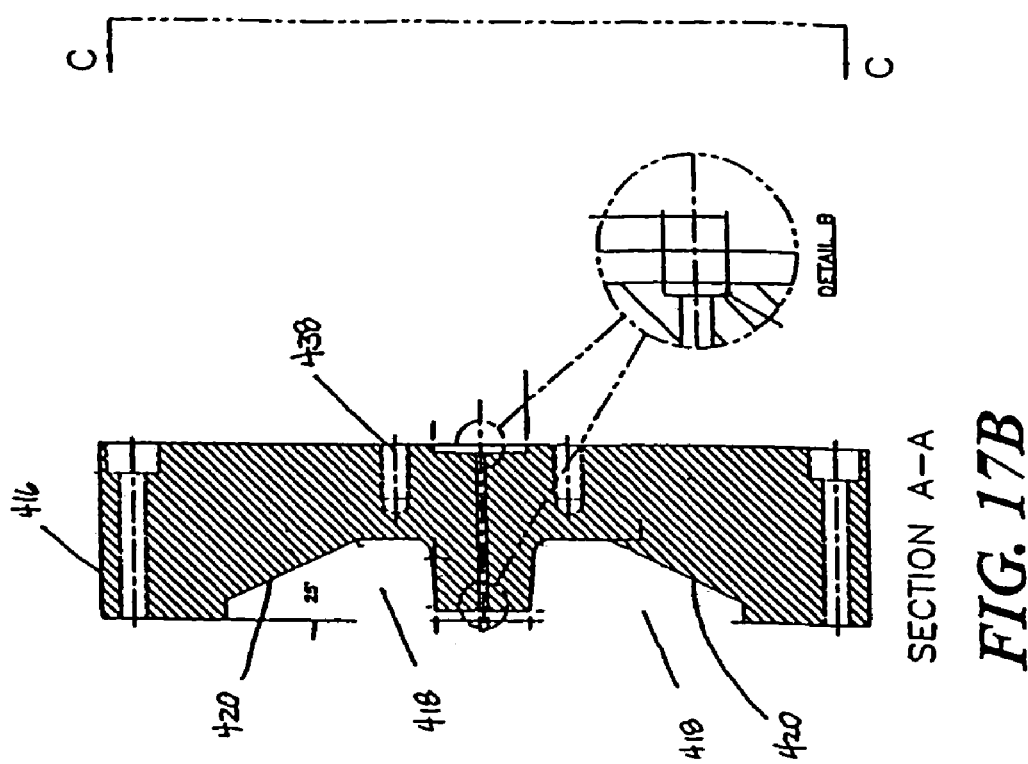
FIGS. 17A and 17B show end and cross-sectional views of one side of a chamber according to the embodiment of the invention shown in FIGS. 15 and 16A-B.
Figure 17A:
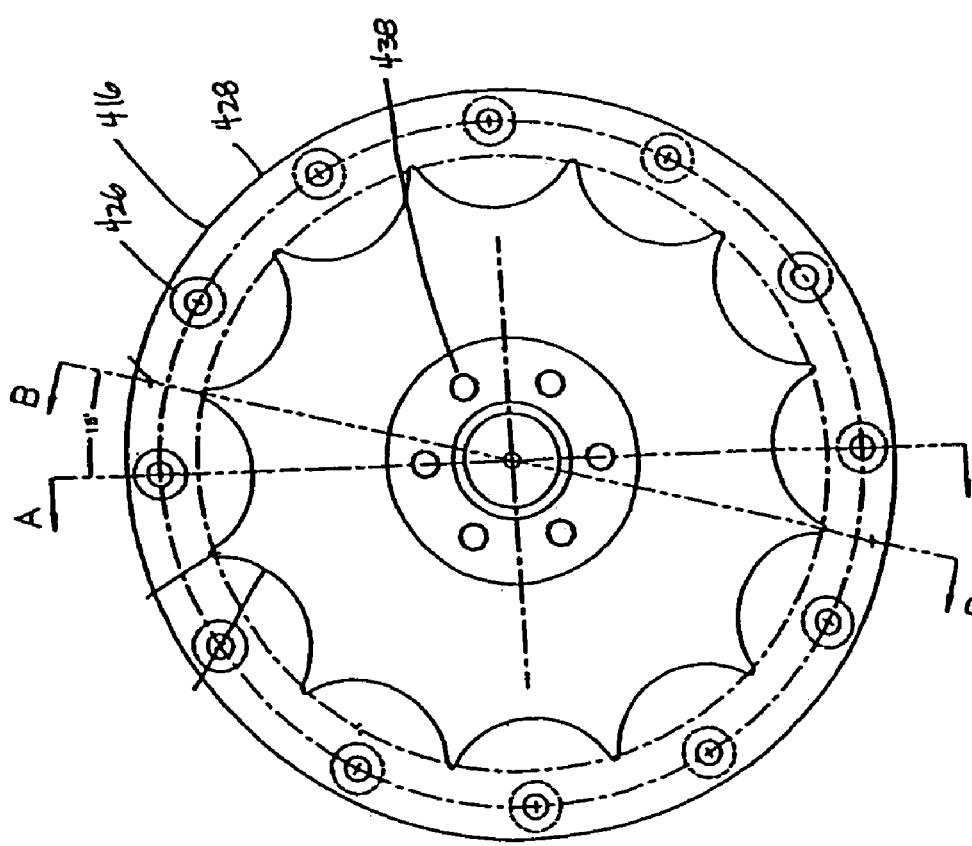

The input cavity. 406 and the output cavity 408 preferably are positioned within the shaft 404 and extend throughout the length of the shaft 404. The injection orifice 410 and the output orifice 412 are in fluid communication with the input cavity 408 and the output cavity 410, respectively, and each orifice contacts an exterior surface of the shaft 406. The CCD 400 further includes at least one injection element 414 which is in fluid communication with the injection orifice 410 and positioned within each chamber 402, as shown in FIGS. 15 and 16A-B. In this embodiment, a plurality of injection elements 414 are shown in FIG. 16A. Additionally, the CCD 400 includes a means for rotating the shaft 404, such as a motor (not shown), and the at least one chamber 402 about the longitudinal axis of the shaft 404.

As shown in FIGS. 15-20, a chamber 402 typically includes two sides 416, which may be composed of a material such as stainless steel. Alternatively, each side 416 may be composed of any material capable of withstanding the stresses developed during operation of the CCD 400, and may include, but is not limited to metals such as iron or titanium, plastics, composites and/or combinations thereof. Note that in this embodiment, when the sides 416 of the chamber 402 are fit together that each chamber 402 has an internal cavity 418 in the shape of a triangular toroid when viewed from the side. Furthermore, the external shape of the chamber 402 is desirably round and wheel-shaped when the two sides 416 are fit together. The outermost portion of the internal cavity 418 maintains an angled portion 420 between each interior surface of the chamber 402 when viewed from a position generally orthogonal to the longitudinal axis of the shaft 404. The angled portion 420 may typically have an angle of about 0 to 90 degrees, and is preferably about 25 degrees.

The angled portion 420 should be such that when the CCD 400 is in operation, a biomaterial (not shown) that is contained within the chamber 402 forms a substantially stationary chromatographic material which does not contact the exterior surface of a manifold sleeve 422 or the shaft 404. Further, the chamber 402 can include a transition section or walls between the angled portion of the chamber and the sleeve or shaft. Typically, the transition section is composed of a surface that is generally orthogonal to the longitudinal axis of the shaft 404. Positioning the transition section in this fashion discourages the biomaterial from contacting the manifold sleeve 422 during operation of the CCD 400 thereby allowing the biomaterial to perform its intended function.

The sides 416 of the chamber 402 are typically fastened together using a plurality of bolts 424. The bolts 424 are positioned within holes 426 located around the perimeter 428 of the chamber 402. Alternatively, each side 416 of the chamber 402 may be held together using any assortment of fasteners or other releasable connection mechanisms. Once the sides 416 of the chamber 402 have been assembled together, the width of the internal cavity 418 of the chamber 402 may be approximately 2.6 inches (6.7 cm) with the diameter of the chamber 402 being approximately 12.0 inches (30.5 cm), and the diameter as measured between opposing bolts 424 is approximately 9.8 inches (25.0 cm). However, other embodiments of the CCD 400 may include a chamber 402 having dimensions in accordance with the scope of this invention, as set forth above.

A seal between each side 416 may be established using an o-ring 430, which is typically positioned on the interior surface of a recessed portion 432 of the internal cavity 418 of the chamber 402. Once the sides 416 are assembled, the o-ring 430 contacts both sides 416. Alternatively, the seal between each side 416 of a chamber 402 may be created using means including, but not limited to, a releasable adhesive, a gasket or any type of sealant material.

As shown in FIGS. 15, 21A-B, 22A-B, the shaft 404 can be divided into two portions that each mount to the chamber 402 at or near the central portion of a respective side 416 of the chamber 402. A flange 434 on each portion of the shaft 404 permits the shaft 404 to connect to the exterior surface of the chamber 402. Bolts 436 are positioned within holes 438 located in the flange 434 and machined into the exterior surface of the chamber 402. Alternatively, the shaft 404 may be secured proximate to the chamber 402 using any assortment of fasteners or other releasable connection mechanisms. Once the shaft 404 has been connected to the sides 416 of the chamber 402, the shaft 404 can then be driven to rotate the shaft 404 which transmits its rotational force through the flange 434 and to the chamber 402.

Referring now to FIGS. 23A-E, a manifold sleeve for a chamber is shown. A chamber 402 may include a manifold sleeve 422 having an input channel 440, at least one output channel 442 in an inner wall of the manifold sleeve 422, a plurality of input apertures 444, and a plurality of output apertures 446 extending between the input channels 440 and output channels 442 respectively and an outer wall of the manifold sleeve 422. Preferably, the input channel 440 is positioned at a midpoint of a longitudinal axis of the manifold sleeve 422. Alternatively, the input channel 440 may be positioned at any point along the longitudinal axis of the manifold sleeve 422. In the preferred embodiment, the input channel 440 is positioned between a plurality of output channels 442. O-rings 448, shown in FIGS. 15 and 16B, are typically located at a recessed edge 450 along the outer wall of the manifold sleeve 422. Furthermore, o-rings 448 may be positioned adjacent to the shaft 402 and around the injection orifice 410 and the output orifice 412. The o-rings 448 provide a seal, to prohibit fluid flow between the shaft 404 and the chamber 402.

The manifold sleeve 422 is positioned in the chamber 402 so that the input channel 440 of the manifold sleeve 422 is in fluid communication with the injection orifice 410 of the shaft 404, and each output channel 442 of the manifold sleeve 422 is in fluid communication with each output orifice 412 located within the shaft 404. In such a position, the o-rings 448 located between the manifold sleeve 422 and the sides 416 of the chamber 402 form a seal which prevents the input fluid from mixing with and contaminating the output fluid. The plurality of input apertures 444 extend from the input channel 440 to the outer wall of the manifold sleeve 422. Similarly, the plurality of output apertures 446 extend from the output channel 442 to the outer wall of the manifold sleeve 422.

The manifold sleeve 422 is sized to fit completely within the chamber 402, once both sides 416 of the chamber 402 have been fastened together. Of course, there are numerous ways to position the manifold sleeve 422 relative or proximate to the shaft 404 as would be understood by one of ordinary skill in the art. Furthermore, it will be understood by one of ordinary skill in the art that there is more than one way to accomplish placing the CCD 400 in fluid communication with a source of input fluid.

From the internal cavity 418 of the chamber 402, as shown in FIGS. 15, 16A-B, and 19B, fluid can exit the chamber 402 via a plurality of chamber output apertures 452. From these apertures 452, fluid travels through a chamber output channel 454 to the output aperture 412 and then through the shaft 404 via the outlet cavity 408, where the fluid can be collected from the CCD 400.

Figure 24:
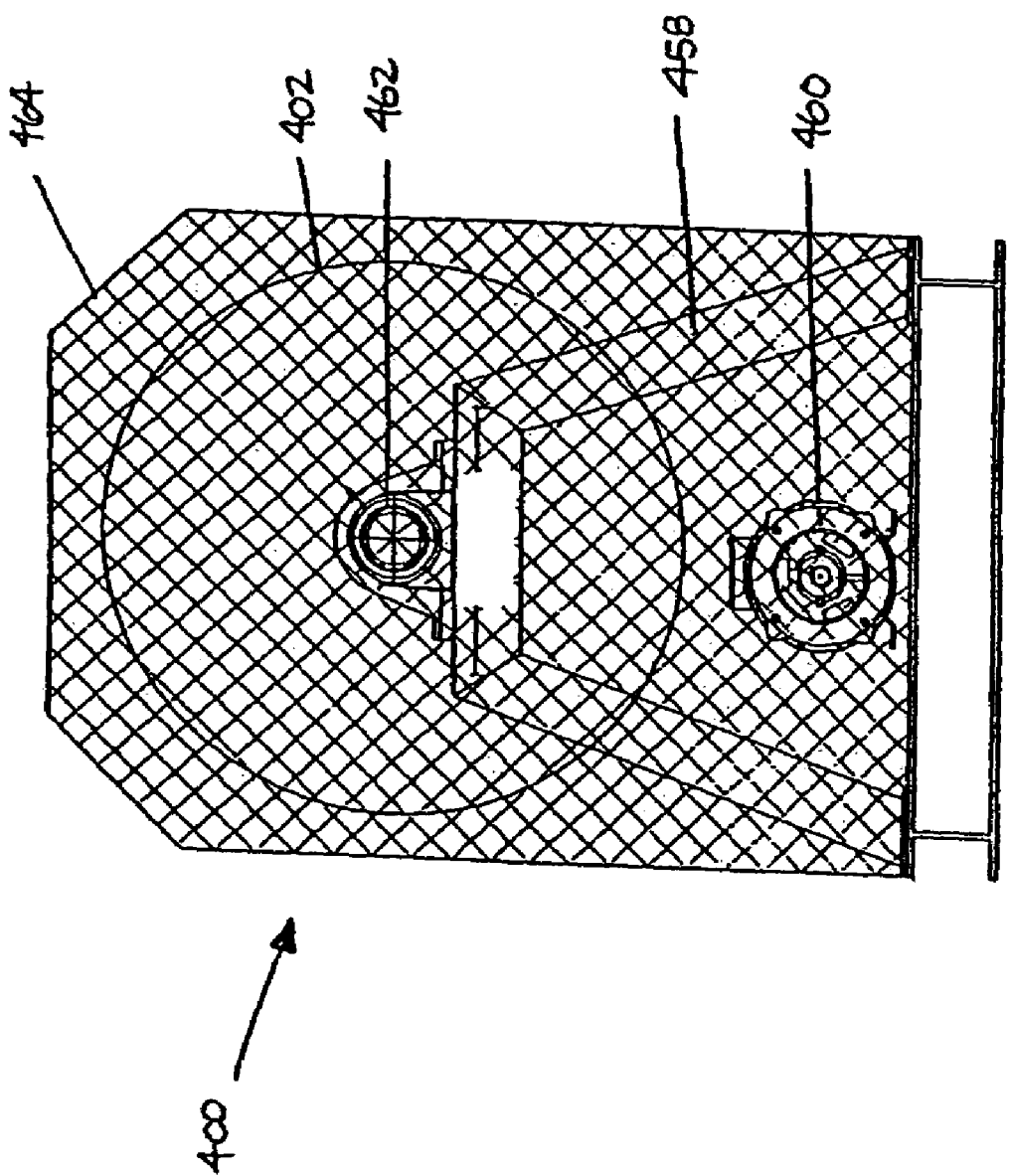
FIG. 24 shows an end view of a CCD according to various embodiments of the invention.

As shown in FIG. 15, the CCD 400 is connected to the shaft 404 with a drive pulley 456. In FIG. 24, the CCD 400 mounts to a stand 458 and a motor 460 is connected via a pulley belt (not shown) to drive the drive pulley 456. The drive pulley 456 is mechanically fastened to the shaft 404, preferably using a weld, an adhesive, a keyway, or other mechanical-type connection. The stand 458 positions the shaft 404 perpendicular to a gravitational force which is typically accomplished by locating the shaft 404 parallel to the Earth's surface. The stand 458 is designed to restrict the shaft 404 from any movement, except rotational movement, about the longitudinal axis of the shaft 404. The stand 458 mounts to bearing assemblies 462 which allow the shaft 404 to rotate while maintaining its position. In operation, the motor 460 is used to rotate the shaft 404 and one or more chambers 402 attached thereto about the longitudinal axis of the shaft 404. The motor 460 is capable of rotating the shaft 404 at any rate desired by the user.

In operation, the chamber 402 houses a chromatographic material, positioned between the exterior surface of the manifold sleeve 422 and the interior surface of the chamber 402. The motor 460, together with the pulley belt and drive pulley 456, rotate the shaft 404 and at least one chamber 402 at a desired rate. As shown in FIG. 24, the CCD 400 typically includes a shield or safety containment chamber 464 which may include two halves and may be hinged or bolted at opposing ends of the stand 458 in order to allow for easy removal of the shield or safety containment chamber 464. The shield or safety containment chamber 464 provides a thermal barrier or heat containment device for maintaining a constant temperature inside the shield or safety containment chamber where the chamber 402 contains the chromatographic material. Furthermore, the shield or safety containment chamber 464 protects individuals from contacting the rotating chambers 402. As the chamber 402 is rotated, pressurized fluid is typically delivered to each chamber 402 via an input feed tube 460, the input cavity 406, the injection orifice 410, the plurality of input apertures 444, the plurality of output apertures 446 and the plurality of injection elements 414. The pressure of the fluid may be monitored using a pressure gauge. The injection elements 414 release the pressurized fluid proximate to the interior surface of the internal cavity 418 of the chamber 402 preferably located the furthest distance from the longitudinal axis of the shaft 404.

After the fluid has been released, the fluid flows from the outermost portion of the internal cavity 418 of the chamber 402 inwardly toward the plurality of chamber output apertures 452 located on the interior cavity 418 of the chamber 402 adjacent to the manifold sleeve 422. When the design of the chamber 402 is a triangular toroid, as set forth above, the fluid injected into the chamber 402 decreases in velocity as it moves from the outermost portion of the internal cavity 418 of the chamber 402 inwardly toward the longitudinal axis of the shaft 404. The velocity of the fluid is reduced because the cross-sectional area of the chamber 402 increases in size moving from the outermost portion of the internal cavity 418 of the chamber 402 toward the longitudinal axis of the shaft 404. Injecting the pressurized fluid at the outermost portion of the internal cavity 418 of the chamber 402 positions the fluid so that it must diffuse through the biomaterial before it leaves the chamber 402 via the plurality of chamber output apertures 452. From these apertures 452, the fluid travels through a chamber output channel 454 to the output aperture 412 and then through the shaft 404 via the outlet cavity 408, where the fluid can be collected from the CCD 400.

The CCD 400, positions and suspends the particles that form a chromatography bed for various beneficial purposes. The CCD 400 may include a particles composed of one or more components capable of performing chromatographical functions or processes.

As mentioned above, the CCD 400 may include a plurality of chambers 402 located adjacent one another on a single shaft 404.

However, the chamber 402 or plurality of chambers 402 may be increased in diameter, while maintaining their triangular toroidal shape, to immobilize and maintain other biomaterials or materials used for chromatographical functions or processes.

Thus, the present invention comprises methods of separation of target molecules comprising compositions comprising chromatography beads, particles, resins or gels that are used in apparatus described herein. Many embodiments are disclosed herein, and combinations of methods, compositions and apparatus are contemplated by the present invention.

As used herein and in the appended claims, the singular forms "a," "an," and "the" include plural reference unless the context clearly indicates otherwise. Thus, for example, reference to a "compound" is a reference to one or more such compounds and includes equivalents thereof known to those skilled in the art, and so forth.

Unless defined otherwise, all technical and scientific terms used herein have the same meaning as commonly understood to one of ordinary skill in the art to which this invention belongs. Although any methods, devices, and materials similar or equivalent to those described herein can be used in the practice or testing of the invention, the preferred methods, devices and materials are now described.

All publications and patents mentioned herein are incorporated herein by reference for the purpose of describing and disclosing, for example, the constructs and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

It is to be understood that this invention is not limited to the particular methodology, protocols, particles, constructs, and reagents described herein and as such may vary. It is also to be understood that the terminology used herein is for the purpose of describing particular embodiments only, and is not intended to limit the scope of the present invention which will be limited only by the appended claims.

EXAMPLE 1

Formation of a Chromatography Bed

An analytical-scale CCD unit equipped with a Model 101096 transparent acrylic immobilization chamber (total volume=30 mL) was loaded with 2 mL of 30 μm diameter glass beads (Cat. No. GP0029, Whitehouse Scientific, UK. The CCD unit was turned on and a RPM of 350 and a flow of 50%-50% (v/v) glycerol-0.01 M sodium phosphate buffer (ph=7.0) was initiated. The physical appearance of the immobilization chamber and its contents could be continuously observed by means of stroboscopic illumination.

At flow rates below 5 mL/min, the glass beads formed a classical packed bed at the long-radius terminal portion of the chamber. As the flow rate was increased to 7 mL/min, the packed bed expanded to an estimated volume of 3 mL and became brighter by visual examination. Stepwise increases in liquid flow rate from 7-12 ml/min resulted in virtually immediate stepwise expansions of the bed volume and an increase in bed brightness. Similarly, stepwise flow rate reductions resulted in bed contraction and appearing to darken. At all flow rates between 7 and 12 mL/min, there was a clearly observable division between the short-radius terminus of the array of glass beads and the flowing liquid exiting the chamber at its short-radius output port.

In order to assess the homogeneity of the bed formed by the method outlined above, the liquid medium was changed to 50%-50% (v/v) glycerol-0.01 M sodium acetate buffer (ph=5.0) and a 2 mL packed bed of glass beads was expanded to an apparent volume of 4 mL, demonstrating that bed fluidization was not dependent on either buffer chemical or liquid pH. Next, a 100 ml quantity of buffer containing 1% Trypan blue was prepared and flowed into the CCD at 7 mL/min. After a short delay, the entrance of the blue-colored liquid medium into the immobilization chamber was observed. The progress of the blue dye front as it migrated anti-radially through the expanded bed could be observed. The progress of the dye front was very regular with no evidence of channeling or other flow irregularities in the fluidized bed.

The ability to expand and contract the glass bead array through multiple cycles by means of flow rate changes at constant RPM and the regularity of the dye penetration of the bed were taken as strong evidence that a classical fluidized bed had been formed.

EXAMPLE 2

Ion Exchange Chromatography

The ability of a bed of 30 μm glass beads immobilized in an analytical-scale CCD unit to exhibit ion-exchange chromatographic properties was assessed in the following manner. The CCD was operated at RPM=350 and a 7 mL/min flow of 50%-50% (v/v) glycerol-0.01 M sodium phosphate buffer (ph=7.0) was initiated after 2 mL of glass beads had been placed in the chamber. After bed formation had been demonstrated (flow rate increased to 10 mL/min; saw subsequent bed volume rise; decreased flow rate to 7 mL/min; saw bed volume lower) a 100 mL quantity of 1% trypan blue in 50%-50% (v/v) glycerol-0.01 M sodium phosphate buffer (ph=7.0) was pumped into the immobilization chamber. As this solution passed through the immobilization chamber, the clear, colorless beads took on a dark blue color. After about 15 min, the liquid flow into the CCD was replaced with 50%-50% (v/v) glycerol-0.01 M sodium phosphate buffer (ph=7.0) without the dye material. The glass bead array was washed clear of unbound dye for an additional 15 min. While the liquid flow into and out of the CCD unit was now clear and colorless, the fluidized bed of glass beads were still darkly stained with bound dye molecules, slightly less darkly than they were prior to the 15 min. wash. Next, the input liquid flow into the CCD was replaced with 50%-50% (v/v) glycerol-0.1 M sodium acetate buffer (ph=5.0). As this solution entered the immobilization chamber, the blue stain on the glass beads began to fade. After 100 mL had flowed through the chamber, the immobilized glass beads were again clear and colorless to the naked eye. These results suggest that the cationic blue dye binds with some affinity to the anionic glass surface at neutral (and likely also at basic) pHs. As the pH of the flowing liquid is lowered, these data show that the increased hydrogen ion concentration in the flowing liquid results in release of the bound dye into the liquid flow.

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, all such arrangements, modifications, and alterations are intended to be within the scope of the appended claims.

What is claimed is:

1. A method for isolating a protein, comprising,
    a) suspending chromatography particles in at least one chamber in a centrifugal force field wherein a continuous flow of a liquid acts to create a force which opposes the centrifugal force field and wherein a gravitational force contributes to the resultant vector summation of all forces acting on the particles, wherein the forces substantially immobilize the particles by the summation of the vector forces acting on the particles, and forming a chromatography bed, wherein each particle is independently suspended without the need for support structure in relation to every other particle to allow for efficient exposure to all surfaces of the particle and the density and shape of the bed may be changed by changing the force parameter on the particles;
    b) adding a heterogeneous liquid comprising a protein,
    c) separating one or more portions of the heterogeneous liquid by the actions of the chromatography bed; and
    d) retaining a separated portion comprising the protein.

2. The method of claim 1, wherein the actions of the chromatography bed separate the protein from the heterogeneous liquid.

3. The method of claim 1, wherein the chromatography particles are adsorbent particles.

4. The method of claim 3, wherein the actions of the chromatography bed separate the heterogeneous liquid by adsorbing the protein to the adsorbent particles.

5. The method of claim 3, wherein the actions of the chromatography bed separate the heterogeneous liquid by allowing materials that are not the protein to pass through the chromatography bed.

6. The method of claim 3, further comprising,
    eluting the retained portion comprising the protein from the adsorbent particles; and
    collecting the eluted protein.

7. The method of claim 3, wherein the chromatography particles are immunoadsorbent particles.

8. The method of claim 1, wherein the chromatography particles comprise, an adsorbent material; a resin; an agarose particle; a silica particle, an ion exchange particle; a gel; a bead, plastics, glass, methacrylate; anionic particles, cationic particles, polar particles, nonpolar particles, hydrophobic particles, hydrophilic particles, ligand exchange particles, ion-pairing particles, size exclusion particles or affinity chromatography particles.

9. The method of claim 1, wherein the heterogeneous liquid comprises a feed stock, tissue extract, chemical reaction mixture, stock broth, bacterial homogenate, bacterial lysate, E. coli inclusion bodies, products secreted from bacteria, yeast, insect, animal, or plant cells, or tissue homogenates of bacteria, yeast, insect, animal, or plant cells, yeast cell homogenates, cellular homogenates, hybridoma fermentation liquids, myeloma cell culture, animal cell culture liquids, milk, animal tissue extracts, plant tissue extracts, unknown source materials, and culture supernatant from a continuous fluidized bed bioreactor.

10. A method for performing chromatography, comprising,
    a) containing chromatography particles in at least one chamber in a centrifugal force field, the chamber having an inlet and an outlet;

b) introducing a heterogeneous liquid to the chamber through the inlet in a liquid stream, wherein a continuous flow of a liquid acts to create a force which opposes the centrifugal force field and wherein a gravitational force contributes to the resultant vector summation of all forces acting on the particles, wherein the forces substantially immobilize the particles by the summation of the vector forces acting on the particles, wherein each particle is independently suspended without the need for support structure in relation to every other particle to allow for efficient exposure to all surfaces of the particle and the density and shape of the bed may be changed by changing the force parameter on the particles;

c) collecting the liquid passing through the chamber and the particles, and d) isolating a protein from either the liquid collected or from the chromatographic particles.

11. The method of claim 10, further comprising, a) providing a second chamber; and b) containing chromatography particles in the second chamber in a centrifugal force field, the chamber having an inlet and an outlet;

c) introducing the collected liquid to the chamber through the inlet in a liquid stream, wherein a continuous flow of a liquid acts to create a force which opposes the centrifugal force field and wherein a gravitational force contributes to the resultant vector summation of all forces acting on the particles, wherein the forces substantially immobilize the particles by the summation of the vector forces acting on the particles;

d) collecting the liquid passing through the second chamber and the particles, e) isolating a protein from either the liquid collected or from the chromatographic particles.

12. The method of claim 10, further comprising, a) providing a second chamber; and b) containing chromatography particles in the second chamber in a centrifugal force field, the chamber having an inlet and an outlet;

c) introducing the heterogeneous liquid to the chamber through the inlet in a liquid stream, wherein a continuous flow of a liquid acts to create a force which opposes the centrifugal force field and wherein a gravitational force contributes to the resultant vector summation of all forces acting on the particles, wherein the forces substantially immobilize the particles by the summation of the vector forces acting on the particles;

d) collecting the liquid passing through the second chamber and the particles, e) isolating a protein from either the liquid collected or from the chromatographic particles.

13. The method of claim 10, further comprising, a) introducing the collected liquid to the chamber through the inlet in a liquid stream, b) collecting the liquid passing through the second chamber and the particles; and c) repeating the introducing and collecting steps until a predetermined amount of desired product is collected.

14. The method of claim 10, further comprising, changing at least one force in at least one chamber to affect either the density or shape of the chromatographic material.

15. The method of claim 10, wherein containing a chromatographic material in at least one chamber comprises containing the chromatographic material in a plurality of chambers.

16. The method of claim 10, wherein the chromatography particles comprise, an adsorbent material; a resin; an agarose particle; a silica particle, an ion exchange particle; a gel; a bead, plastics, glass, methacrylate; anionic particles, cationic particles, polar particles, nonpolar particles, hydrophobic particles, hydrophilic particles, ligand exchange particles, ion-pairing particles, size exclusion particles or affinity chromatography particles.

17. The method of claim 10, wherein the heterogeneous liquid comprises a purified feed stock, tissue extract, stock broth, bacterial homogenate, bacterial lysate, *E. coli* inclusion bodies, products secreted from bacteria, yeast, insect, animal, or plant cells, or tissue homogenates of bacteria, yeast, insect, animal, or plant cells, yeast cell homogenates, cellular homogenates, whole hybridoma fermentation liquid, myeloma cell culture, whole animal cell culture liquid, milk, animal tissue extracts, plant tissue extracts, unknown source materials, chemical reaction mixtures, and culture supernatant from a continuous fluidized bed bioreactor.

* * * * *